US009901347B2

(12) United States Patent
Van Dam et al.

(10) Patent No.: US 9,901,347 B2
(45) Date of Patent: Feb. 27, 2018

(54) BILIARY SHUNTS, DELIVERY SYSTEMS, AND METHODS OF USING THE SAME

(75) Inventors: Jacques Van Dam, San Carlos, CA (US); Chris Julian, Los Gatos, CA (US); Marc Kreidler, Sunnyvale, CA (US); Eric Knisley, Weston, FL (US); James Craig Milroy, Palo Alto, CA (US); Robert Matthew Ohline, Redwood City, CA (US); Charles Swinehart, San Jose, CA (US)

(73) Assignee: TERUS MEDICAL, INC., Redwood City, CA (US)

( * ) Notice: Subject to any disclaimer, the term of this patent is extended or adjusted under 35 U.S.C. 154(b) by 0 days.

(21) Appl. No.: 12/791,816

(22) Filed: Jun. 1, 2010

(65) Prior Publication Data

US 2011/0054381 A1    Mar. 3, 2011

Related U.S. Application Data

(60) Provisional application No. 61/182,280, filed on May 29, 2009.

(51) Int. Cl.
*A61M 1/00* (2006.01)
*A61B 17/11* (2006.01)
*A61F 2/04* (2013.01)
*A61M 27/00* (2006.01)

(52) U.S. Cl.
CPC ............ *A61B 17/1114* (2013.01); *A61F 2/04* (2013.01); *A61M 27/002* (2013.01); *A61B 2017/1139* (2013.01); *A61F 2002/041* (2013.01)

(58) Field of Classification Search
USPC .......................................................... 604/8
See application file for complete search history.

(56) References Cited

U.S. PATENT DOCUMENTS

| 2,127,903 A | 8/1938 | Bowen |
| 3,385,300 A | 5/1968 | Holter |
| 3,818,511 A | 6/1974 | Goldberg et al. |
| 3,834,394 A | 9/1974 | Hunter et al. |

(Continued)

FOREIGN PATENT DOCUMENTS

| CN | 1220590 A | 6/1999 |
| EP | 0779062 A1 | 6/1997 |

(Continued)

OTHER PUBLICATIONS

International Preliminary Report on Patentability for PCT/US2010/057736 dated Jun. 6, 2013.

(Continued)

*Primary Examiner* — Todd J Scherbel
*Assistant Examiner* — Guy K Townsend
(74) *Attorney, Agent, or Firm* — Maschoff Brennan

(57) ABSTRACT

The application discloses devices, delivery tools, systems, and methods for treating biliary disease. Device comprise, for example, a component configured for deployment between a gallbladder and location within a gastrointestinal tract of a patient which has a proximal end and a distal end with a lumen extending therethrough. A method of deploying the device can be achieved by, for example, creating a duct or fistula between a gallbladder lumen and a portion of a gastrointestinal tract; and providing for drainage from the gallbladder to the gastrointestinal tract.

18 Claims, 16 Drawing Sheets

(56) References Cited

U.S. PATENT DOCUMENTS

| | | | |
|---|---|---|---|
| 3,933,040 A | 1/1976 | Thompson | |
| 4,085,757 A | 4/1978 | Pevsner | |
| 4,263,917 A | 4/1981 | Moss | |
| 4,352,358 A | 10/1982 | Angelchik | |
| 4,699,611 A * | 10/1987 | Bowden | A61F 2/04 604/105 |
| 4,781,677 A | 11/1988 | Wilcox | |
| 4,900,303 A | 2/1990 | Lemelson | |
| 4,955,859 A | 9/1990 | Zilber | |
| 4,966,294 A | 11/1990 | Salama | |
| 4,968,294 A * | 11/1990 | Salama | A61F 2/0009 128/DIG. 25 |
| 4,994,066 A | 2/1991 | Voss | |
| 5,071,419 A | 12/1991 | Rydell et al. | |
| 5,159,925 A | 11/1992 | Neuwirth et al. | |
| 5,167,614 A | 12/1992 | Tessmann et al. | |
| 5,170,805 A | 12/1992 | Kensey et al. | |
| 5,171,311 A | 12/1992 | Rydell et al. | |
| 5,197,948 A | 3/1993 | Ghodsian | |
| 5,201,746 A | 4/1993 | Schichman | |
| 5,259,847 A * | 11/1993 | Trambert | A61F 2/94 604/164.1 |
| 5,261,920 A * | 11/1993 | Main | A61B 17/115 227/175.1 |
| 5,270,805 A | 12/1993 | Kensey et al. | |
| 5,334,210 A | 8/1994 | Gianturco | |
| 5,364,400 A | 11/1994 | Rego et al. | |
| 5,454,788 A | 1/1995 | Walker et al. | |
| 5,443,449 A | 8/1995 | Buelna | |
| 5,466,242 A | 11/1995 | Mori | |
| 5,499,994 A | 3/1996 | Tihon et al. | |
| 5,514,088 A | 5/1996 | Zakko | |
| 5,536,248 A * | 7/1996 | Weaver | A61M 25/0026 604/506 |
| 5,632,762 A | 5/1997 | Myler | |
| 5,643,254 A | 7/1997 | Scheldrup | |
| 5,709,224 A | 1/1998 | Behl et al. | |
| 5,741,333 A | 4/1998 | Frid | |
| 5,743,905 A | 4/1998 | Eder | |
| 5,755,769 A | 5/1998 | Richard et al. | |
| 5,769,880 A | 6/1998 | Truckai et al. | |
| 5,776,126 A | 7/1998 | Wilk | |
| 5,800,341 A | 9/1998 | McKenna et al. | |
| 5,817,046 A | 10/1998 | Glickman | |
| 5,824,071 A | 10/1998 | Nelson et al. | |
| 5,853,419 A | 12/1998 | Imran | |
| 5,860,426 A | 1/1999 | Kleiman | |
| 5,876,432 A | 3/1999 | Lau et al. | |
| 6,019,757 A | 2/2000 | Scheldrup | |
| 6,077,261 A | 6/2000 | Behl et al. | |
| 6,165,210 A | 12/2000 | Lau et al. | |
| 6,241,762 B1 | 6/2001 | Shanley | |
| 6,245,101 B1 | 6/2001 | Drasler et al. | |
| 6,246,914 B1 | 6/2001 | de la Rama et al. | |
| 6,283,992 B1 | 9/2001 | Hankh et al. | |
| 6,312,404 B1 | 11/2001 | Agro et al. | |
| 6,348,066 B1 | 2/2002 | Pinchuk et al. | |
| 6,358,247 B1 | 3/2002 | Altman et al. | |
| 6,406,491 B1 | 6/2002 | Vanney | |
| 6,409,755 B1 | 6/2002 | Vrba | |
| 6,416,545 B1 | 7/2002 | Mikus et al. | |
| 6,468,303 B1 | 10/2002 | Amplatz et al. | |
| 6,544,291 B2 | 4/2003 | Taylor | |
| 6,558,429 B2 | 5/2003 | Taylor | |
| 6,585,754 B2 | 7/2003 | Wallace | |
| 6,599,299 B2 | 7/2003 | Schultz | |
| 6,610,100 B2 | 8/2003 | Phelps et al. | |
| 6,616,675 B1 | 9/2003 | Evard | |
| 6,641,610 B2 | 11/2003 | Wolf et al. | |
| 6,655,386 B1 | 12/2003 | Makower et al. | |
| 6,663,663 B2 | 12/2003 | Kim et al. | |
| 6,746,489 B2 | 6/2004 | Dua et al. | |
| 6,764,519 B2 | 7/2004 | Whitmore, III | |
| 6,945,949 B2 | 9/2005 | Wilk | |
| 6,949,080 B2 * | 9/2005 | Wolf | A61B 5/0031 424/426 |
| 6,962,602 B2 | 11/2005 | Vardi et al. | |
| 6,964,681 B2 | 11/2005 | Murray, III | |
| 7,004,949 B2 | 2/2006 | Yencho et al. | |
| 7,011,095 B2 | 3/2006 | Wolf et al. | |
| 7,041,110 B2 | 5/2006 | Yencho et al. | |
| 7,094,260 B2 | 8/2006 | Jing et al. | |
| 7,118,600 B2 | 10/2006 | Dua et al. | |
| 7,144,363 B2 | 12/2006 | Pai et al. | |
| 7,182,744 B2 * | 2/2007 | Yamasaki | A61B 17/00491 128/898 |
| 7,294,115 B1 | 11/2007 | Wilk | |
| 7,634,319 B2 | 12/2009 | Schneider et al. | |
| 7,641,645 B2 | 1/2010 | Schur | |
| 7,645,259 B2 | 1/2010 | Goldman | |
| 7,647,891 B2 | 1/2010 | Anderson et al. | |
| 7,670,364 B2 | 3/2010 | Dusbabek et al. | |
| 7,704,223 B2 | 4/2010 | Mantell | |
| 7,704,245 B2 | 4/2010 | Dittman et al. | |
| 7,717,871 B2 | 5/2010 | Odland | |
| 7,717,936 B2 | 5/2010 | Keating et al. | |
| 7,722,629 B2 | 5/2010 | Chambers | |
| 7,727,225 B2 | 6/2010 | Broaddus et al. | |
| 2001/0044647 A1 | 11/2001 | Pinchuk et al. | |
| 2002/0032487 A1 | 3/2002 | Dua et al. | |
| 2002/0055768 A1 | 5/2002 | Hess et al. | |
| 2002/0095110 A1 | 7/2002 | Vanney et al. | |
| 2002/0156523 A1 | 10/2002 | Lau et al. | |
| 2003/0045828 A1 | 3/2003 | Wilk | |
| 2003/0055484 A1 | 3/2003 | Lau et al. | |
| 2003/0069533 A1 | 4/2003 | Kakutani et al. | |
| 2003/0069606 A1 | 4/2003 | Girouard et al. | |
| 2003/0083734 A1 | 5/2003 | Friedrich et al. | |
| 2003/0149472 A1 | 8/2003 | Pinchuk et al. | |
| 2003/0163079 A1 | 8/2003 | Burnett | |
| 2003/0216733 A1 | 11/2003 | McClurken et al. | |
| 2004/0073317 A1 | 4/2004 | Schultz | |
| 2004/0093058 A1 | 5/2004 | Cottone et al. | |
| 2004/0102855 A1 | 5/2004 | Shank | |
| 2004/0181150 A1 | 9/2004 | Evans et al. | |
| 2004/0199262 A1 | 10/2004 | Dua et al. | |
| 2004/0211434 A1 | 10/2004 | Loomas et al. | |
| 2004/0215331 A1 | 10/2004 | Chew et al. | |
| 2004/0249335 A1 | 12/2004 | Faul et al. | |
| 2004/0249470 A1 | 12/2004 | Whitmore, III | |
| 2005/0010275 A1 | 1/2005 | Sahatjian et al. | |
| 2005/0010280 A1 | 1/2005 | Jing et al. | |
| 2005/0021084 A1 | 1/2005 | Lu et al. | |
| 2005/0107733 A1 | 5/2005 | Faul et al. | |
| 2005/0137707 A1 | 6/2005 | Malek | |
| 2005/0149166 A1 | 7/2005 | Schaeffer et al. | |
| 2005/0159726 A1 | 7/2005 | Evans et al. | |
| 2005/0171598 A1 | 8/2005 | Schaeffer | |
| 2005/0192659 A1 | 9/2005 | Dahl et al. | |
| 2005/0216074 A1 | 9/2005 | Sahatjian et al. | |
| 2005/0228413 A1 | 10/2005 | Binmoeller | |
| 2005/0273060 A1 | 12/2005 | Levy et al. | |
| 2005/0277964 A1 | 12/2005 | Brenneman et al. | |
| 2005/0277965 A1 | 12/2005 | Brenneman et al. | |
| 2006/0047337 A1 | 3/2006 | Brenneman | |
| 2006/0058864 A1 | 3/2006 | Schaeffer et al. | |
| 2006/0085034 A1 * | 4/2006 | Bettuchi | A61B 17/115 606/219 |
| 2006/0106455 A1 | 5/2006 | Furst et al. | |
| 2006/0129221 A1 | 6/2006 | Heruth | |
| 2006/0135963 A1 * | 6/2006 | Kick | A61B 17/221 606/108 |
| 2006/0155369 A1 | 7/2006 | Edwin et al. | |
| 2006/0235269 A1 | 10/2006 | Waxman | |
| 2006/0247575 A1 | 11/2006 | Cartledge et al. | |
| 2007/0016306 A1 | 1/2007 | Dua et al. | |
| 2007/0021828 A1 | 1/2007 | Krolik et al. | |
| 2007/0038283 A1 | 2/2007 | Mustapha | |
| 2007/0043381 A1 | 2/2007 | Moszner et al. | |
| 2007/0043391 A1 | 2/2007 | Moszner et al. | |
| 2007/0055358 A1 | 3/2007 | Krolik et al. | |
| 2007/0067011 A1 | 3/2007 | Krolik et al. | |
| 2007/0073376 A1 | 3/2007 | Krolik et al. | |

(56) References Cited

U.S. PATENT DOCUMENTS

| | | | |
|---|---|---|---|
| 2007/0073388 A1 | 3/2007 | Krolik et al. | |
| 2007/0088425 A1 | 4/2007 | Schaeffer | |
| 2007/0173867 A1 | 7/2007 | Brenneman | |
| 2007/0173921 A1 | 7/2007 | Wholey et al. | |
| 2007/0179592 A1 | 8/2007 | Schaeffer | |
| 2007/0225634 A1 | 9/2007 | Ferren et al. | |
| 2007/0249985 A1 | 10/2007 | Brenneman et al. | |
| 2007/0293940 A1 | 12/2007 | Schaeffer et al. | |
| 2008/0195171 A1 | 8/2008 | Sharma | |
| 2008/0243151 A1 | 10/2008 | Binmoeller | |
| 2009/0143713 A1 | 6/2009 | Van Dam et al. | |
| 2009/0143759 A1 | 6/2009 | Van Dam et al. | |
| 2009/0143760 A1 | 6/2009 | Van Dam et al. | |
| 2009/0264808 A1* | 10/2009 | Young ............... | A61M 27/002 604/8 |
| 2009/0306633 A1 | 12/2009 | Trovato et al. | |
| 2010/0010293 A1* | 1/2010 | Sato .................. | A61B 17/3478 600/101 |
| 2010/0274085 A1* | 10/2010 | Mugan ............ | A61B 17/22032 600/115 |
| 2011/0054381 A1 | 3/2011 | Van Dam et al. | |
| 2011/0071350 A1 | 3/2011 | Van Dam et al. | |
| 2011/0071566 A1 | 3/2011 | Dam et al. | |

FOREIGN PATENT DOCUMENTS

| | | |
|---|---|---|
| EP | 1044663 A2 | 10/2000 |
| EP | 1044663 A3 | 3/2001 |
| EP | 1314404 A2 | 5/2003 |
| EP | 1314404 A3 | 9/2003 |
| EP | 1795151 A1 | 6/2007 |
| GB | 2460287 A | 11/2009 |
| JP | 03-9746 A | 1/1991 |
| JP | 11076412 | 3/1999 |
| JP | 15-116982 | 4/2003 |
| RU | 2226364 C1 | 4/2004 |
| SU | 620262 | 8/1978 |
| SU | 688185 | 9/1979 |
| SU | 1131498 | 12/1984 |
| SU | 1586687 | 8/1990 |
| SU | 1634257 | 3/1991 |
| SU | 1828745 | 7/1993 |
| WO | WO 96/13296 A1 | 5/1996 |
| WO | WO 97/27898 A1 | 8/1997 |
| WO | WO-97/38637 A1 | 10/1997 |
| WO | WO 00/12832 A2 | 3/2000 |
| WO | WO 00/18325 A | 4/2000 |
| WO | WO 00/12832 A3 | 6/2000 |
| WO | WO 01/58384 A1 | 8/2001 |
| WO | WO-2004/069097 | 8/2004 |
| WO | WO 2006/062996 A2 | 6/2006 |
| WO | WO 2006/127784 A2 | 11/2006 |
| WO | WO 2007/005010 A1 | 1/2007 |
| WO | WO 2007/014283 A2 | 2/2007 |
| WO | WO 2006/127784 A3 | 5/2007 |
| WO | WO 2007/050628 A2 | 5/2007 |
| WO | WO 2007/050628 A3 | 1/2008 |
| WO | WO 2006/062996 A3 | 4/2009 |
| WO | WO 2007/014283 A3 | 4/2009 |
| WO | WO 2009/073507 A2 | 6/2009 |
| WO | WO 2009/073507 A3 | 6/2009 |
| WO | WO 2009/073515 A2 | 6/2009 |
| WO | WO 2009/073515 A3 | 6/2009 |
| WO | WO 2009/073521 A2 | 6/2009 |
| WO | WO 2009/073521 A3 | 6/2009 |
| WO | WO-2012/071031 | 5/2012 |

OTHER PUBLICATIONS

British Search Report received for related British Application No. 0821930.5 dated Mar. 19, 2009.

European Supplementary Search Report for European Patent Application No. 08856414.1 dated Feb. 29, 2012.

International Search Report and Written Opinion for counterpart International Patent Application No. PCT/US2010/057736 dated Feb. 28, 2012.

International Search Report and Written Opinion for International Patent Application No. PCT/US2008/084830 dated Jun. 24, 2009.

International Search Report and Written Opinion for International Patent Application No. PCT/US2008/084865 dated Jun. 24, 2009.

International Search Report and Written Opinion for International Patent Application No. PCT/US2008/084888 dated Jul. 17, 2009.

* cited by examiner

BILIARY SHUNTS, DELIVERY SYSTEMS, AND METHODS OF USING THE SAME

CROSS-REFERENCE

The present application claims the benefit of U.S. Provisional Patent Application No. 61/182,280, filed on May 29, 2009, entitled "Biliary Shunts, Delivery Systems, and Methods of Using the Same" the disclosure of which is incorporated herein by reference in its entirety.

The present application has related subject matter to U.S. Utility patent application Ser. No. 12/277,491, filed on Nov. 25, 2008, and International Application No. PCT/US2008/84888, filed on Nov. 26, 2008, entitled "Biliary Shunts, Delivery Systems, Methods of Using the Same, and Kits Therefor" by Jacques Van Dam, J. Craig Milroy, and R. Matthew Ohline; U.S. Utility patent application Ser. No. 12/277,443, filed on Nov. 25, 2008, and International Application No. PCT/US2008/84830, filed on Nov. 26, 2008, entitled "Methods, Devices, Kits and Systems for Defunctionalizing the Gallbladder" by Jacques Van Dam, J. Craig Milroy, and R. Matthew Ohline; and U.S. Utility patent application Ser. No. 12/277,338, filed on Nov. 25, 2008, and International Application No. PCT/US2008/84865, filed on Nov. 26, 2008, entitled "Methods, Devices, Kits and Systems for Defunctionalizing the Cystic Duct" by Jacques Van Dam, J. Craig Milroy, and R. Matthew Ohline. The aforementioned applications are incorporated herein by reference in their entirety.

FIELD OF THE INVENTION

The invention described in this patent application addresses challenges confronted in the treatment of biliary disease. Biliary disease includes conditions affecting the gallbladder, cystic duct, and common bile duct.

Biliary System Function and Anatomy:

Bile is a greenish-brown digestive fluid produced by the liver 10 illustrated in FIGS. 1-2, and is vital for the digestion of fatty foods. Bile is secreted by liver cells and collected by a network of ducts that converge at the common hepatic duct 12. While a small quantity of bile drains directly into the lumen of the duodenum 30 (the section of small intestine immediately downstream of the stomach), most travels through the common hepatic duct 12 and accumulates in the lumen of the gallbladder 14. Healthy gallbladders are pear-shaped sacs with a muscular wall that, on average, measure 10 cm in length and can store approximately 50 ml of fluid within its lumen. When fatty foods are ingested, the hormone cholecystokinin (CCK) is released, which causes the gallbladder 14 to contract. Contraction of the gallbladder 14 forces bile to flow from the gallbladder 14, through the cystic duct 16, into the common bile duct 18, out the papilla 28, and finally into the duodenum 30 of the small intestine. Here, it mixes and reacts with the food that exits the stomach (chyme). The Sphincter of Oddi 26 controls secretions from the liver 10, pancreas 24, and gallbladder 14 into the duodenum 30 of the small intestine. The opening on the inside of the descending duodenum 30 after the Sphincter of Oddi 26 is called the major duodenal papilla 28 (of Vater). Together, the biliary ducts, the gallbladder 14, the cystic duct 16 and the common bile duct 18 comprise the biliary system (FIG. 1).

The pancreas 24 is a gland organ in the digestive and endocrine system of vertebrates. It is both an endocrine gland (producing several important hormones, including insulin, glucagon, and somatostatin), as well as an exocrine gland, secreting pancreatic juice containing digestive enzymes that pass to the small intestine. These enzymes help in the further breakdown of the carbohydrates, protein, and fat in the chyme. The pancreatic duct 22, or duct of Wirsung, is a duct joining the pancreas 24 to the common bile duct 18 to supply pancreatic juices which aid in digestion provided by the exocrine pancreas. The pancreatic duct 22 joins the common bile duct 18 just prior to the major duodenal papilla 28, after which both ducts perforate the medial side of the second portion of the duodenum 30 at the major duodenal papilla 28.

Biliary Disease:

The most common problem that arises in the biliary system is the formation of gallstones, a condition called cholelithiasis. Approximately 20 million Americans have gallstones, and about 1-3% will exhibit symptoms in any given year. In the U.S., gallstones are more common among women, with 25% of women having gallstones by the age of 60 and 50% by the age of 75. Pregnancy and hormone replacement therapy increase the risk of forming gallstones. Prevalence is lower for American men: approximately 25% will develop gallstones by the age of 75. In the U.S., gallstones are responsible for the highest number of hospital admissions due to severe abdominal pain.

Gallstones 20, 20' (FIG. 2) are most often composed of cholesterol, but may also be formed from calcium bilirubinate, in which case they are called pigment stones. They range in size from a few millimeters to several centimeters, and are irregularly shaped solids resembling pebbles. They can form in the gallbladder 14, cystic duct 16, and/or the common bile duct 18. By themselves, gallstones do not necessarily result in disease states. This is the case 90% of the time. However, stones can cause infection and inflammation, a condition known as cholecystitis, which is generally the result of restricting or blocking the flow of bile from the gallbladder 14 and common bile duct 18, or the fluids secreted by the pancreas 24.

Gallbladder disease may be chronic, and patients who suffer from this may periodically experience biliary colic. Symptoms include pain in the upper right abdomen near the ribcage, nausea, and/or vomiting. The pain may resolve within an hour of onset, may prove unresponsive to over-the-counter medicines, and may not decrease with changes of position or the passage of gas. Recurrence is common, with pain often recurring at the same time of day, but with frequency of less than once per week. Fatty or large meals may cause recurrence several hours after eating, often awakening the patient at night. Patients may elect to suffer from these symptoms for very long periods of time, such as years or even decades.

Patients with chronic cholecystitis have gallstones and low-grade inflammation. Untreated, the gallbladder 14 may become scarred and stiff over time, leading to a condition called dysfunctional gallbladder. Patients who have chronic cholecystitis or dysfunctional gallbladder may experience gas, nausea, and abdominal discomfort after meals, and chronic diarrhea.

Acute cholecystitis (a surgical emergency) develops in 1-3% of those with symptomatic gallstone disease, and is due to obstruction of the common bile duct 18 or cystic duct 16 by stones or sludge. Symptoms are similar to biliary colic, though they are more severe and persistent. Pain in the upper right abdomen can be constant and severe, the intensity may increase when drawing breath, and it may last for days. Pain may radiate to the back, under the breastbone or the shoulder blades, and it may be perceived on the left side of the abdomen. In addition to nausea and vomiting, one third of patients experience fever and chills. Complications from acute cholcystitis can be serious and life threatening, and include gangrene, abscesses, perforation of the gallbladder 14 which can lead to bile peritonitis, pus in the gallbladder wall (empyema), fistulae, and gallstone ilius (when a gallstone creates a blockage in the small intestine).

When gallstones 20' become lodged in the common bile duct 18 (FIG. 2), the condition is known as choledocholithiasis. Symptoms for this condition include pain, nausea and vomiting, and some patients develop jaundice, have dark urine and/or lighter stools, rapid heartbeat, and experience an abrupt drop in blood pressure. These symptoms can also be accompanied by fever, chills, and/or severe pain in the upper right abdomen. Complications from choledocholithiasis can also be very serious, and include infection of the common bile duct 18 (cholangitis) and inflammation of the pancreas 24 (pancreatitis).

A smaller patient population suffers from gallbladder disease that occurs in the absence of gallstones. This condition, called acalculous gallbladder disease, can also be chronic or acute. Chronic acalculous gallbladder disease, also called biliary dyskinesia, is thought to be caused by motility disorders that affect the gallbladder's ability to store and release bile. Acute acalculous gallbladder disease occurs in patients who suffer from other serious illnesses which can lead to inflammation of the gallbladder 14 because of a reduction in the supply of blood to the gallbladder 14 or a reduced ability to contract and empty bile into the duodenum 30.

Cancer can also develop in the gallbladder 14, though this condition is rare. Gallstones have been found in 80% of patients with gallbladder cancer. Gallbladder cancer typically develops from polyps, which are growths inside the gallbladder 14. When polyps 15 mm across or larger are observed, the gallbladder is removed as a preventive measure. Polyps smaller than 10 mm are widely accepted as posing low risk and are not generally removed. When detected early, before the cancer has spread beyond the mucosa (inner lining) of the gallbladder, the 5-year survival rate is approximately 68%. However, gallbladder cancer is not usually detected until patients are symptomatic, by which time the disease is more advanced.

Treatment of Biliary Disease:

The most effective treatment for biliary disease has been surgical removal of the gallbladder 14, a procedure called cholecystectomy. Surgical removal of the gallbladder 14 is indicated for patients who experience a number of less severe gallstone attacks, cholecystitis, choledocholithiasis, pancreatitis, acalculous biliary pain with evidence of impaired gallbladder 14 emptying, those at high risk for developing gallbladder cancer, and those who have previously undergone endoscopic sphincterotomy for common bile duct stones. Other treatment modalities exist and are frequently used, but gallbladder disease tends to recur in the majority of patients who forgo cholecystectomy and pursue alternatives. Removal of the gallbladder 14 is highly successful at permanently eliminating biliary disease. Cholecystectomy is one of the most commonly performed procedures on women. The gallbladder 14 is not an essential organ, and after a period of adjustment post surgery, patients tend to return to more or less normal digestive function.

Cholecystectomy can be performed either as open surgery, which requires a single larger incision in the upper right abdomen, or laparoscopic surgery, in which several small instruments are inserted through much smaller incisions in the abdomen. Approximately 80% of cholecystectomies are performed laparoscopically. The primary benefits of this minimally invasive approach are faster recovery for the patient, and a reduction in overall healthcare costs. Patients who receive laparoscopic cholecystectomy are usually released the same day. By contrast, patients receiving open cholecystectomies typically spend 5-7 days in a hospital before release. 5-10% of laparoscopic procedures convert to open procedures when difficulties arise, such as injury to major blood vessels, inadequate access, inadequate visualization, previous endoscopic sphincterotomy, and thickened gallbladder wall. Complications from cholecystectomy (open or laparoscopic) include bile duct injuries (0.1-0.5% for open, 0.3-2% with a declining trend for laparoscopic), pain, fatigue, nausea, vomiting, and infection. In up to 6% of cases, surgeons fail to identify and remove all gallstones present.

In some cases, the degree of infection and inflammation prevents patients from undergoing immediate cholecystectomy. In these cases, the gallbladder 14 must be treated with antibiotics and anti-inflammatory agents, and drained through a tube into a reservoir outside the abdomen. Placement of this tube occurs in a procedure called percutaneous cholecystostomy, in which a needle is introduced to the gallbladder 14 through the abdomen, fluid is withdrawn, and a drainage catheter is inserted. This catheter drains into an external bag which must be emptied several times a day until the tube is removed. The drainage catheter may be left in place for up to 8 weeks. In cases where no drainage catheter is inserted, the procedure is called gallbladder aspiration. Since no indwelling catheter is placed, the complication rate for gallbladder aspiration is lower than that of percutaneous cholecystostomy.

Treatment methodologies other than cholecystectomy include expectant management, dissolution therapy, endoscopic retrograde cholangiopanctreatograpy (ERCP) with endoscopic sphincterotomy, and extracorporeal shockwave lithotripsy (ESWL).

Expectant management is appropriate for patients who have gallstones but no symptoms, and for non-emergency cases with less severe symptoms. This approach is not recommended when patients are in high risk categories (e.g. high risk for gallbladder cancer) or have very large gallstones (e.g. greater than 3 cm).

Oral dissolution therapy involves the administration of pills containing bile acids that can dissolve gallstones. This approach is only moderately effective, and the rate of recurrence of gallstones after completion of treatment is high. It is not appropriate for patients with acute inflammation or stones in the common bile duct (more serious conditions). Dissolution therapy tends to be more effective for patients with cholesterol stones, and is sometimes used in conjunction with lithotripsy. Despite its relative ineffectiveness, it is costly: treatment can last up to 2 years and the drugs cost thousands of dollars per year.

Related to oral dissolution therapy is contact dissolution, a procedure that involves injection of a solvent such as methyl tert-butyl ether (MTBE) directly into the gallbladder 14. This approach is highly effective at dissolving gallstones, but patients may experience severe burning pain.

ERCP (endoscopic retrograde cholangiopancreatograpy) is a procedure in which an endoscope is introduced through the mouth of a patient, past the stomach to the papilla 28 (FIG. 2), where the common bile duct 18 empties into the duodenum 30. The overall goal of the procedure is to insert instruments and tools into the common bile duct 18 via the papilla 28 in order to treat biliary disease. Typically, endoscopic sphincterotomy is performed, which is a procedure that enlarges the opening of the papilla 28 in the small intestine. This can be accomplished surgically or via balloon dilation. Contrast agent is introduced into the common bile duct 18 to visualize the biliary tree fluoroscopically. Tools for clearing blockages, such as mechanical lithotripsy devices, can be deployed to crush gallstones and remove the resulting debris. Drainage catheters and stents may also be inserted to facilitate the drainage of bile past obstructions. Complications from this challenging procedure occur at a rate of 5-8%, and include recurrence of stone formation, pancreatitis, infection, bleeding, and perforation.

Extracorporeal shockwave lithotripsy (ESWL) is a technique in which focused, high-energy ultrasound is directed at the gallbladder 14. The ultrasound waves travel through the soft body tissue and break up the gallstones. The resulting stone fragments are then usually small enough to pass through the bile duct into the small intestine. Oral dissolution therapy is often used in conjunction with ESWL. This treatment is not in common use, as less than 15% of the patient population are good candidates. However, ESWL is used to treat patients who are not candidates for surgery. Complications from ESWL include pain in the gallbladder area, pancreatitis, and failure of the gallstone fragments to pass into the small intestine.

SUMMARY OF THE INVENTION

An aspect of the disclosure is directed to devices for treating biliary disease. Suitable devices comprise a component configured for establishing fluid communication between a gallbladder and a target location within a gastrointestinal tract of a mammal, the component having a proximal end and a distal end with a lumen extending therethrough, a tubular section with a radially extending proximal flange and a radially extending distal flange wherein at least one of the proximal flange and distal flange is disc shaped and at least one of the proximal flange and the distal flange has a plurality of radially extending elements. The devices can be configured for deployment by an endoscope, a needle, a guidewire, a guidance catheter, and/or a dilatation balloon. Endoscopes can further be adapted to comprise an ultrasound device. A system for treating biliary disease is also contemplated which comprises a device for configuring a duct between a gallbladder and a gastrointestinal tract of a patient having a proximal end and a distal end with a lumen extending therethrough between. In some aspects the devices can be configured to further comprise a delivery mechanism for delivering a substance. Deployment of these devices can, in some instances, cause a conduit to be formed between a gallbladder lumen and a target location within the gastrointestinal tract.

Another aspect of the disclosure is directed to a biliary disease treatment device comprising: a component configured for establishing fluid communication between a gallbladder and a target location within a gastrointestinal tract of a mammal, the component having a proximal end and a distal end with a lumen extending therethrough, a tubular section with a radially extending proximal flange and a radially extending distal flange wherein at least one of the proximal flange and distal flange is disc shaped and at least one of the proximal flange and the distal flange has a plurality of radially extending elements. The conduit can, for example, be formed between a lumen of the gallbladder and a target location within the gastrointestinal tract, such as proximal to a duodenum.

Still another aspect of the disclosure is directed to devices for treating biliary disease. Suitable devices comprise a component configured for establishing fluid communication between a gallbladder and a target location within a gastrointestinal tract of a mammal, the component having a proximal end and a distal end with a lumen extending therethrough, a tubular section with a radially extending proximal flange and a radially extending distal flange wherein at least one of the proximal and distal flange is comprised of a first material and the tubular section is comprised of a second material. The devices can be configured for deployment by an endoscope, a needle, a guidewire, a guidance catheter, and/or a dilatation balloon. Endoscopes can further be adapted to comprise an ultrasound device. A system for treating biliary disease is also contemplated which comprises a device for configuring a duct between a gallbladder and a gastrointestinal tract of a patient having a proximal end and a distal end with a lumen extending therethrough between. In some aspects the devices can be configured to further comprise a delivery mechanism for delivering a substance. Deployment of these devices can, in some instances, cause a conduit to be formed between a gallbladder lumen and a target location within the gastrointestinal tract.

Devices according to any one of the configurations disclosed can be formed from a bioresorbable material. Moreover, the devices can be removable and/or expandable. The devices can also be configurable in one or more configurations selected from a deployment configuration, a delivery configuration and a final configuration. Moreover, the devices can be configured such that a profile of the device changes between said configurations. Additionally, or in the alternative, a cross-sectional area of the device can be variable along a length of the devices. In some configurations a component or implant can be configured such that it has a flareable end, suitable flareable ends include ends that are generally hemispherical. Additionally, components or implants can comprise a configurable retainable feature. In some aspects, components or implants can comprise one or more clips configured to secure the components or implants at one or more positions. In some configurations, one or more fenestrations may be provided. Moreover, the lumen or conduit can be configurable to provide restrictable fluid flow or to provide for a valve, such as a flow-restrictor or one-way valve. Any of the configurations of the device can be constructed such that the device is flexible. The system or device can also be configured to include a generally elongate tube that is adapted and configured to extend into the gastrointestinal tract. Configurations that include an elongate tube can be configured such that the tube is patent at a first end; the patent first end can be for placement adjacent the gallbladder. In still other configurations, the elongate tube is not patent at a second end. Moreover, the tube can be configured such that it has an adjustable length. Additionally, one or more fluid control components can be provided to the designs. Additionally, an enlargeable portion comprising two or more legs can be provided.

Another aspect of the disclosure is directed to a kit for treating biliary disease comprising a duct forming component positioned between a gallbladder and a gastrointestinal tract. The kit can comprise any of the devices or systems described herein. Additionally, compounds can be provided for delivery to a tissue. Compounds or materials include, but are not limited to, for example, one or more of each of sclerosing agents, antibiotics, inflammatory agents, anti-inflammatory agents, biocompatible gels, and biocompatible foams. Additionally, a catheter, guidewire, needle, guidance catheter or balloon catheter can be provided. In some aspects, the kit can also include an ablation device. Additional components of the kits include, for example, one or more of each of a pair of scissors, a scalpel, a swab, a syringe, a hemostat, a lubricant, a needle, a snare, an antiseptic, and an anesthetic.

Yet another aspect of the disclosure is directed to a method for treating biliary disease. A method of treating biliary disease comprises: (a) using an endoscope to place at least one of a guidewire, a needle, a guidance catheter, and a dilatation catheter between an access lumen in a body and a gallbladder; (b) inserting a delivery catheter over the at least one of guidewire, needle, guidance catheter, and dilatation catheter and into the gallbladder; (c) delivering a component configured for establishing fluid communication between a gallbladder and a target location within a gastrointestinal tract of a mammal, the component having a proximal end and a distal end with a lumen extending therethrough, a tubular section with a radially extending proximal flange and a radially extending distal flange wherein at least one of the proximal flange and distal flange is disc shaped and at least one of the proximal flange and the distal flange has a plurality of radially extending elements; and (d) positioning the component between the access lumen in the body and the gallbladder to create a lumen therebetween. Additionally, the method can comprise the step of delivering a substance to the gallbladder via the duct. Additional method steps include delivering a device to the gallbladder through the duct. Suitable devices to be delivered include one or more of a stent, a drug-coated stent, a catheter, a needle, a guidance catheter, a balloon dilatation catheter and/or a guidewire. In some cases, the step of creating the duct further comprises the step of inserting a device in communication between the gastrointestinal tract and the gallbladder lumen. The step of creating the duct between a gallbladder lumen and a portion of a gastrointestinal tract can further comprise the step of inserting a conduit between the gallbladder lumen and the portion of the biliary system. In some aspects, the method further comprises the step of forming a biological duct in situ from a patient's tissue. As will be appreciated by those skilled in the art, the step of inserting a conduit between the gallbladder lumen and the portion of the gallbladder tract can occur at a first time and the step of forming the biological duct in situ from the patient's tissue occurs at a second time remote from the first time. Moreover the methods can further comprise the step of providing a seal to prevent fluid from leaking into a peritoneum. Additionally the gallbladder can be defunctionalized in situ, such as by delivering a substance or material into a space within the gallbladder. Suitable substances or materials include, but are not limited to, gels and foams. In some instances, the delivered substances can be activated in situ. Additionally, an amount of material can be delivered to fill, or substantially fill, the gallbladder lumen. Additionally, in some instances, the step of defunctionalizing is achieved by one or more of sclerosing or necrotizing a tissue within the gallbladder which can, for example, be achieved by an ablation technique.

Still another aspect of the disclosure is directed to a method of delivering a device to treat biliary disease comprising: (a) using an endoscope to place a guidewire between an access lumen in a body and a gallbladder; (b) inserting a delivery catheter over the guidewire and into the gallbladder; (c) delivering a conduit on the catheter; and (d) positioning the conduit between the access lumen in the body and the gallbladder to create a lumen therebetween. The methods can also include the step of forming a biological duct in situ from a patient's tissue. Additionally, the step of positioning the conduit can occur at a first time and the step of forming the biological duct in situ from the patient's tissue occurs at a second time remote from the first time. Some methods can further comprise the step of passively retaining a distal end of the guidewire in the gallbladder while the guidewire is used to deliver additional elements. In some instances, the methods include the step of retaining a distal end of the guidewire within the gallbladder. In some methods, gallstones are removed through the created lumen. In other methods, a substance is delivered to the gallbladder via the created lumen. In some instances, the substance occupies the gallbladder lumen and can be one or more of antibiotics, inflammatory agents, and anti-inflammatory agents. Methods may also include preventing bile from entering the or a gallbladder lumen. Additionally, the gallbladder may be localized via endoscopic ultrasound, in some instances. Moreover, it may be useful to access the gallbladder via the gastrointestinal tract. A suitable location for accessing the gallbladder via the gastrointestinal tract would be to access the gallbladder at a duodenum. With any of the methods it may be desirable to alter and/or remove gallstones. Moreover, other obstructions within the biliary system can also be removed. The delivered conduit can be, for example, one or more of a stent, and a drug-coated stent. In some applications of the methods, biliary disease is treated without removal of the gallbladder. In still other applications of the method, a treatment area is visualized as part of the method. In some methods, the conduit is anchored in place. In still other methods, the conduit is changed from a delivery configuration to a deployment configuration, from a delivery configuration to a final configuration or from a deployment configuration to a final configuration. Still other methods provide for reducing a cross-sectional profile of the conduit, providing a seal to prevent fluid from leaking into a peritoneum, and/or restricting fluid flow from the gallbladder lumen to the gastrointestinal tract. Other methods include operating a valve to restrict fluid flow.

Still another aspect of the disclosure is directed to a conduit. The conduit can be formed such that is comprises: a shape memory wire configured for establishing fluid communication between a gallbladder and a target location within a gastrointestinal tract of a mammal, the shape memory wire being shaped to form a proximal end and a distal end with a lumen extending therethrough, a tubular section with a radially extending proximal flange and a radially extending distal flange. Thus, the conduit is formed from a bioresorbable material. Additionally, the conduit can be one or more of removable or expandable. Conduit configurations can be selected from a deployment configuration, a delivery configuration and a final configuration. Typically the conduit also comprises a variable profile and/or has a cross-sectional area that is variable along its length. Moreover, the can be configured for deployment by at least one of an endoscope, a needle, a guidewire, a guidance catheter and a dilatation catheter. Additionally, the conduit can have a flareable end, be flexible, have an adjustable length, be at least partially from a shape memory material, be adapted and configured to engage a tubular valve member within a lumen, and/or have one or more retaining features adapted and configured to retain the conduit in situ, or any combination thereof.

In still other aspects, a conduit is provided that comprises: one or more rings at a proximal end and a distal end with adapted and configured to engage a compliant material forming a substantially tubular structure therethrough. The conduit can be formed from a bioresorbable material, can be configured to be flexible, removeable and/or expandable, to have one or more configurations selected from a deployment configuration, a delivery configuration and a final configuration, to have a variable profile and/or a cross-sectional area that is variable along a length, an adjustable length or combinations thereof. Additionally, the conduit can be configured for deployment by at least one of an endoscope, a needle, a guidewire, a guidance catheter and a dilatation catheter. The conduit can also be configured at least partially from a shape memory material. Additionally, one or more retaining features adapted and configured to retain the conduit in situ.

Yet other aspects of the disclosure include a delivery catheter comprising: delivery catheter comprising: a control handle, an elongate flexible shaft, a central rod, and a delivery element having a first conduit retaining component and a second conduit retaining element wherein a portion of a conduit is clamped between the retaining components during delivery, and released when the first retaining component is moved away from the second retaining component to release a conduit held on a distal end of the delivery catheter.

Still another delivery catheter comprises a control hand, an elongate flexible shaft, a central rod, and a at least one dilating electrosurgical electrode. At least one of a leading edge electrode can be provided and/or one or more radially arranged dilating electrodes. The dilating electrodes can be positionable to optimize a size of a resulting aperture.

A delivery catheter comprising a central member adapted and configured to move a distal end of the catheter relative to a coaxial sheath, further having one or more flexible members can also be provided. The flexible members can be configured to have one or more hinges adapted and configured to reduce strain. Moreover, the flexible hinges can expand outward to anchor and retain the delivery catheter within a lumen. Thus, for example, the flexible members are configurable into an umbrella shape. The flexible members can further define a work space when opened.

A delivery catheter tool channel device can be provided that comprises a tubular structure adapted and configured to securely engage a distal end of a delivery catheter. The tool can further be configured to comprise a proximal end and a distal end with a central aperture adapted and configured to be positioned over the distal end of the delivery catheter. An elongate aperture positioned off center the elongated device can also be provided for receiving additional tools or components. In at least some configurations one or more apertures positioned through the main body of the tool is provided.

A delivery catheter tool channel device comprising a first component adapted and configured to securely fit within a channel of a delivery catheter, and a second component adapted and configured to provide an aperture through which a secondary device can be positioned wherein the first and second component are connected via a bridging mechanism can also be provided.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention will be set forth with particularity in any claims presented based on this application. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
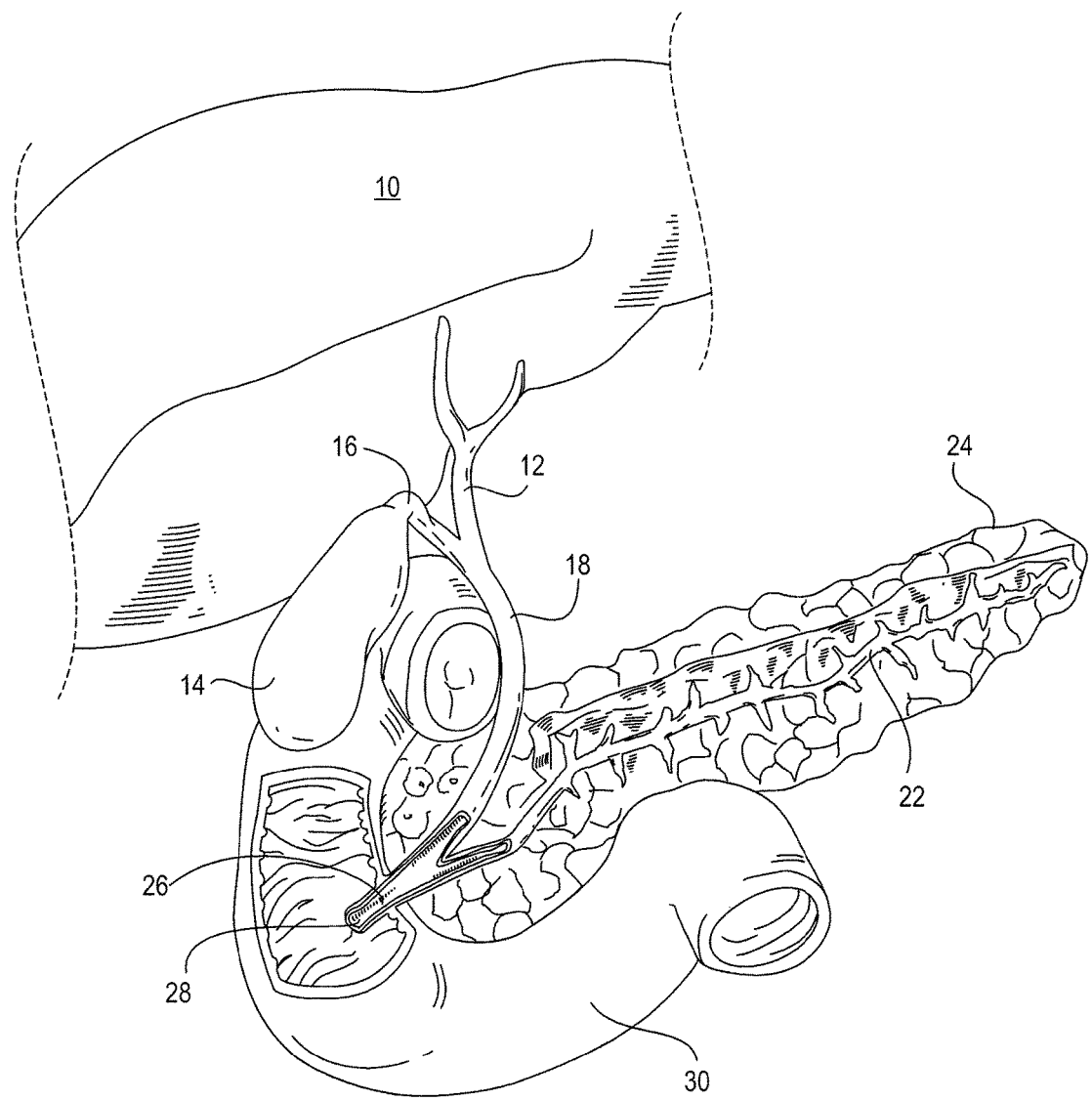
FIG. 1 illustrates an overview of the biliary system.

Devices, systems, methods and kits provided herewith can obviate the need for a plurality of procedures, including, for example: 1) percutaneous cholecystostomy, 2) cholecystectomy, 3) percutaneous trans-hepatic cholangiography (PTHC), and 4) endoscopic retrograde cholangiopancreatography (ERCP). Additionally, disclosed treatment modalities enable treatment of a distal common bile duct 18 obstruction, e.g. secondary to pancreatic carcinoma, cholagiocarcinoma, and/or ampullary carcinoma. As will be appreciated by those skilled in the art, the conventional standard of care for treating biliary disease has been surgical removal of the gallbladder 14 and closure of the cystic duct 16. While this has proven to be an effective mechanism for permanently eliminating biliary disease and its recurrence, the present invention seeks to accomplish the same end in a less invasive and less costly way. This may be achieved by treating biliary disease without requiring the removal of the gallbladder 14. Methods and apparatus are described in this application that are intended to effectively treat biliary disease with the gallbladder 14 and cystic duct 16 left in situ by providing a shunt to the gallbladder that enables fluid communication, or selective fluid communication, from the gallbladder, e.g., fluid can drain from the gallbladder into the small intestine via the shunt.

A method of treating biliary disease involves using an endoscope 310 to access a region 350 in the gastrointestinal (GI) tract (FIG. 3) to which the gallbladder 14 is in close proximity, locating the gallbladder 14, accessing the gallbladder, and then treating the underlying condition that led to the need for intervention. As will be appreciated by those skilled in the art, as a result of variations in anatomy, the actual location of the target region Treatments may also include, but are not limited to: providing for drainage of the gallbladder 14 and/or the biliary tree, delivering suitable materials or substances, such as antibiotics, inflammatory, anti-inflammatory agents (any of which may be short-term acting, fast acting, or time release), and/or other substances (e.g. adhesives, bioadhesives, etc.) to the gallbladder 14 and/or biliary tree, removing gallstones 20, facilitating the destruction and subsequent removal of gallstones, clearing obstructions, delivering catheters, delivering stents (drug coated or not drug coated), temporarily or permanently defunctionalizing the cystic duct 16, temporarily or permanently defunctionalizing the gallbladder 14. Devices and therapies can be delivered in a single treatment, with minimal likelihood of or necessity for follow-up or repeat procedures.

The gallbladder can be accessed by any suitable mechanism or procedure including, percutaneously, endoscopically, laparascopically, and the like. Moreover, any of the materials and substances delivered to the gallbladder can be delivered concurrently or sequentially. Delivery of substances can occur sequentially in time or the sequence of delivery can be separated by seconds, minutes, or hours.

Figure 3:
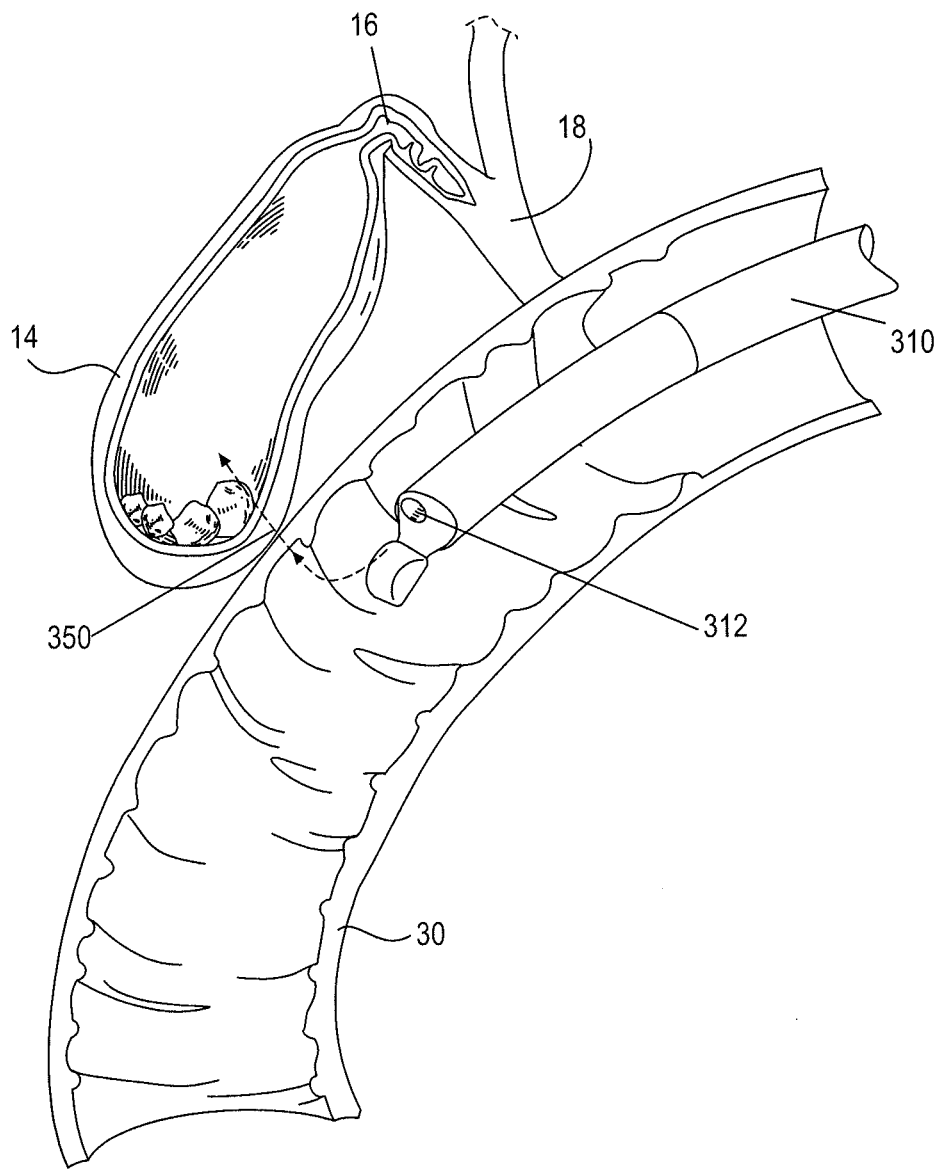
FIG. 3 illustrates the distal end an endoscope positioned within a mammalian body accessing the biliary system via the intestinal system.

Localization of the gallbladder 14 can be performed via endoscopic ultrasound (EUS) by accessing the wall of the GI tract with an endoscope 310 as shown in FIG. 3. Localization may also be achieved by any other method that visualizes anatomical features, such as fluoroscopy, x-rays, magnetic resonance imaging (MRI), computed axial tomography (CT) scans, ultrasound imaging from outside the body, or any method of anatomical imaging and visualization.

Once the gallbladder 14 has been located, it may be accessed and/or treated at the target region or site 350 through the wall of the GI tract (or any lumen in proximity to the gallbladder 14) with tools and devices (e.g. needles, guidewires, guidance catheters, dilators, etc.) delivered through, for example, an endoscope 310. Such tools and devices may be inserted down the length of the endoscope's working channel 312, or loaded onto or near the distal end of the endoscope 310. Alternately, tools and other devices may be used that do not require the aid of the endoscope for navigation or delivery. Direct visualization may be provided by the endoscope 310 during the procedure, as well as irrigation, suction, and insufflation.

Though the preferred location for accessing the gallbladder lumen is the duodenum 30, it may also be readily achieved through the wall of other regions of the GI tract, such as the stomach or the jejunum, for example. Thus, any lumen in close proximity to the gallbladder 14 is a candidate for access to and treatment of the gallbladder 14 and other members of the biliary system.

Description of the Devices:

In the present invention, in situ treatment of the gallbladder 14 is enabled via the creation of a passageway between the gallbladder lumen and a lumen in close proximity, e.g. at or near the duodenum. This passageway or duct may be created by an implantable device 420, such as that illustrated in FIG. 4.

The passageway may be temporary or permanent. It may be thought of as a fistula that is intentionally created between the gallbladder 14 and another lumen in proximity to the gallbladder, as described above. Alternately, it may be thought of as a stoma between the gallbladder 14 and another lumen in proximity. The passageway serves as a conduit, an access port, through which a number of actions may be accomplished, drainage may be achieved, and treatments may be delivered.

A device 420 forming the passageway may be left in the patient for a short period of time, such as a few hours, a few days or a few weeks, or it may be left in place for extended periods of time, such as several weeks, months, or years. The device 420 may also be left in place permanently. If it is left in place long-term, tissue may form around the device 420, creating a fistula that connects the gallbladder 14 to the access lumen which may persist even if the passageway device 420 is removed, thus forming a biological in situ device 420 from the patient's own tissue. The fistula may be beneficial and useful, as it may continue to allow drainage for the contents of the gallbladder 14 into the small intestine. It may provide either the primary or a secondary mechanism for delivering bile into the digestive system, for example. It may also provide convenient access in cases where repeated treatments are required. Though there may be no need to close the resulting fistula, it may also be closed at any time by a clinician should this become desirable. After removal of a device 420 that initially formed the passageway, a fistula may remain open for a period of time and then close on its own, and may pose no additional risk and prove to be an acceptable course of events. Whether the device 420 is left in place or removed, and whether the fistula is left open or closed, evidence at the site may serve to mark the location of treatment in the event of future procedures.

To facilitate delivery and deployment of a device 420, it may be useful to reconfigure its shape. For example, the cross-sectional area presented by the device 420 at various locations may be reduced, thus, for example, reducing its overall profile. In cases where the configuration of the device 420 is caused to change, it may be helpful to conceive of the device 420 having one or more configurations, for example: one configuration when it is delivered (a "delivery configuration"), another configuration when it is deployed (a "deployment configuration"), and yet another configuration when it is in place and functional (a "final configuration" or "functional configuration"). Still other configurations may also be necessary or useful. For the delivery configuration, it may be advantageous to alter (e.g. reduce) the cross-sectional area or profile, so that it more easily fits delivery mechanisms, such as the working channel of an endoscope 310 (illustrated in FIG. 3). During deployment, the configuration of the device 420 may be altered so that placement into the patient is facilitated. This may be different from both the delivery configuration and the final configuration, though this is not necessarily the case. As will be appreciated by those skilled in the art, one or more configurations can be the same or substantially the same.

Figure 2:
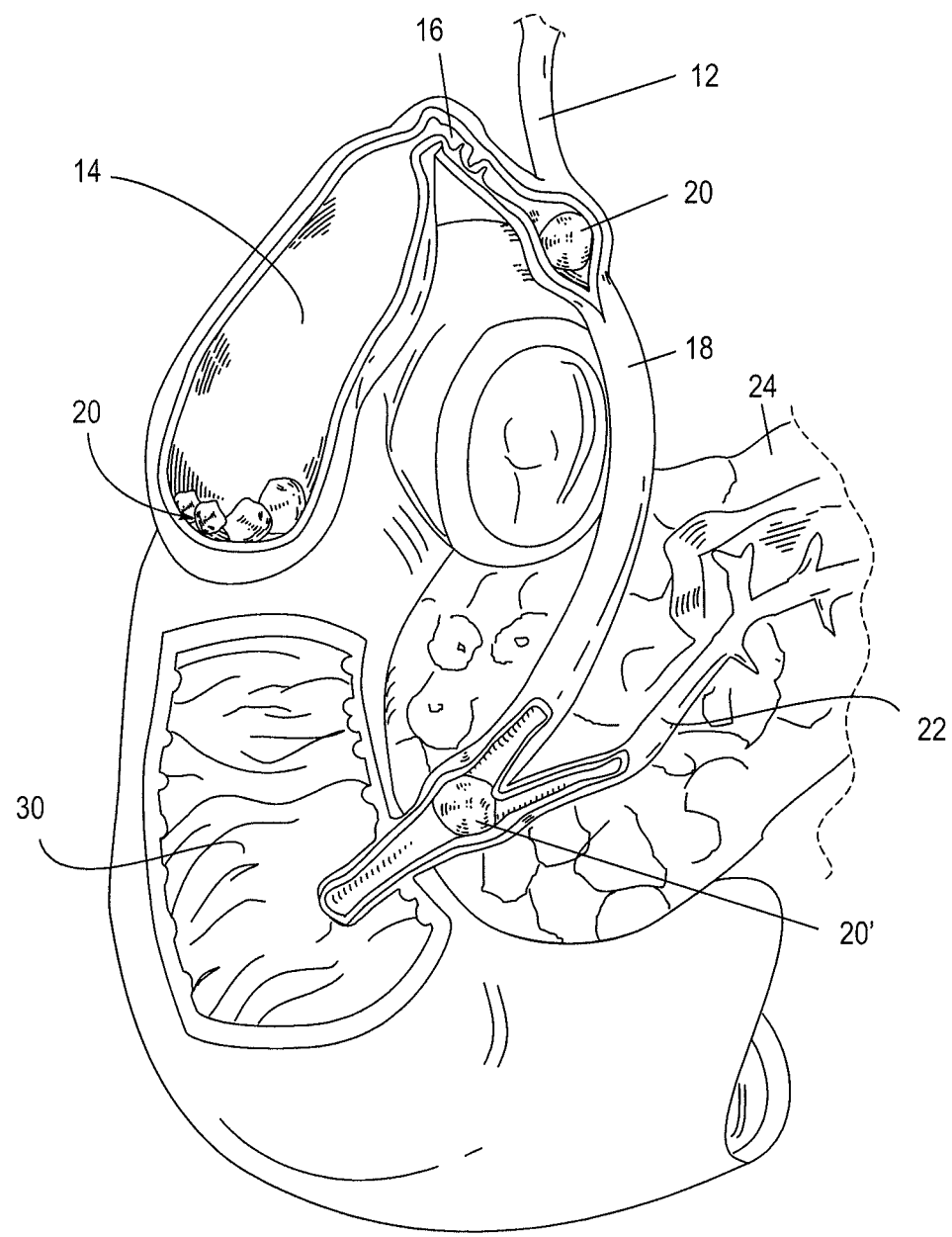
FIG. 2 illustrates the biliary system with gallstones.
Figure 4:
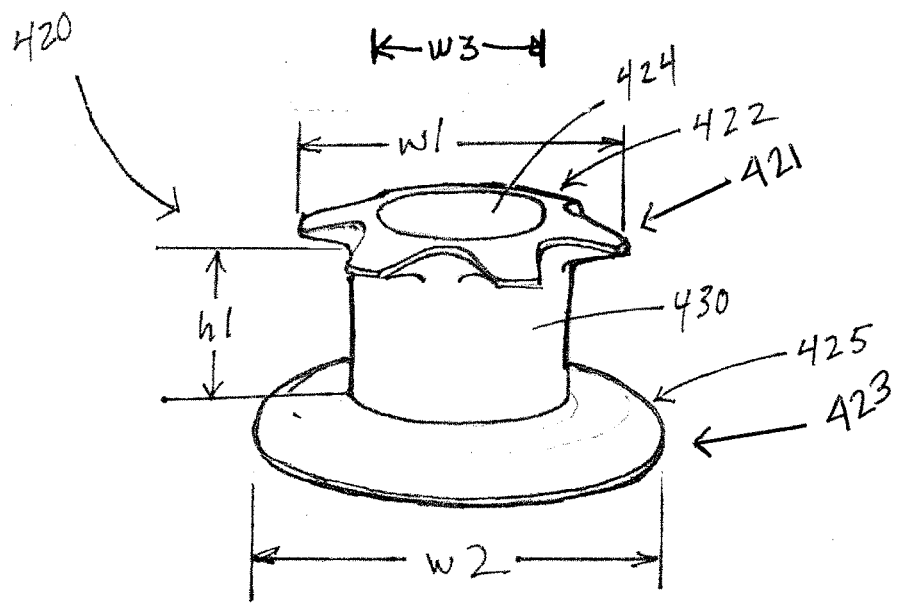
FIG. 4 illustrates an embodiment of a device adapted to provide a conduit between two body lumens.

Description of the Conduit:

The preferred embodiment of the conduit is that of a short tube that has flared tissue retention features at both ends, as depicted in FIG. 4, which secure the conduit device 420 in the desired location within the gallbladder 14 and the access lumen, e.g. the duodenum 30. The conduit 420 forms the proposed passageway 424 between the gallbladder 14 and the body lumen from which it will be accessed, such as through the duodenum 30 (FIG. 2). A tubular portion 430 (FIG. 4) of the conduit 420 is typically about 4-10 mm in length h1, with a first diameter w1 of the device large enough to facilitate drainage and access, typically in the range of 2-10 mm. However, other dimensions can be used without departing from the scope of the invention. A second diameter w2 of the tubular portion 430 of the conduit 420 is typically larger than about 3 mm (10 French) in its final configuration. The device has an inner diameter w3 which defines a lumen or passageway 424 through the device from a first end 421 to a second end 423. The passageway 424 enables fluid communication from one end of the device to the other end of the device. The shape of the retention features may be the same on both ends, or they may be different on either end, as is shown in FIG. 4, where the distal end 422 is divided into at least one finger so that it resembles a star shape and the proximal end 425 is substantially a flat disc-like element with gentle curved features at the edges so that the device is atraumatic to adjacent tissue. Dividing a retaining feature into at least one finger facilitates folding the features forward or backward so that the profile of the device may be reduced for delivery. The conduit may be constructed from any suitable material (e.g. silicone, urethane, polyurethane, Teflon, TFE, PTFE, ePTFE, Nitinol, stainless steel, etc.), however a soft durometer molded silicone material is preferred in this embodiment.

Figures 5A, 5B:
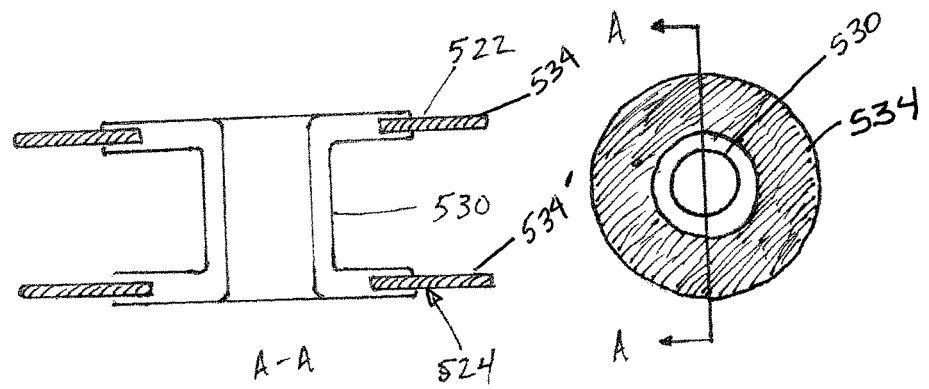
FIGS. 5A-B illustrates another embodiment of the device comprised of more than one material.

Another embodiment, shown in FIGS. 5A-B in a section view and a top view, is a multi-component assembly comprised of more than one material. In the embodiment shown, a soft pliable material (e.g. a low durometer silicone) comprises a tubular portion 530 of the conduit, and is attached to a dissimilar material which forms the flared retaining feature 534, 534' at either the distal end 522, the proximal end 524, or both ends. The materials may be attached by any suitable mechanisms, elements, means or design features that secure the ends together. Alternatively, other materials may be used to attach them such as adhesives, clips, clamps, or other hardware components.

Figure 6A:
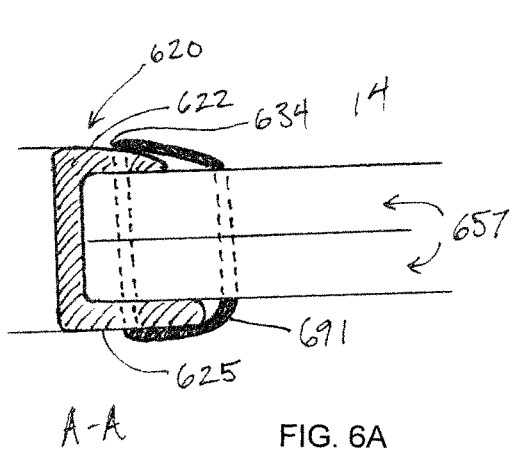
FIGS. 6A-D illustrates an embodiment of the device retained with suture or T-tags.
Figure 6B:
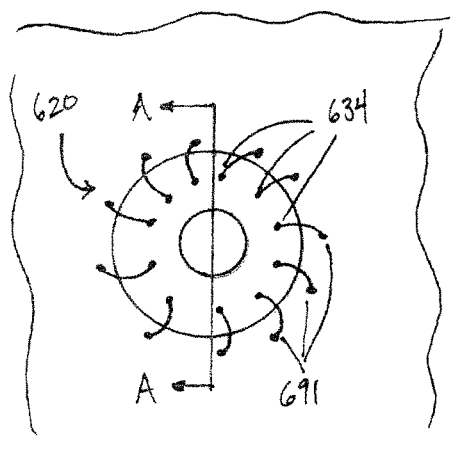
Figure 6C:
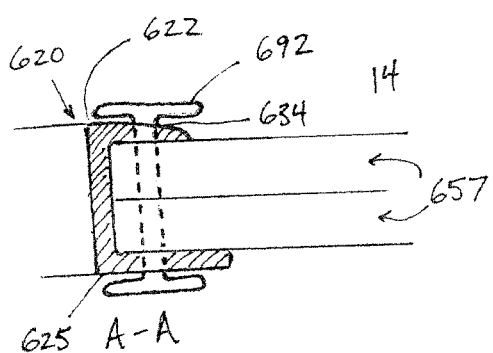
Figure 6D:
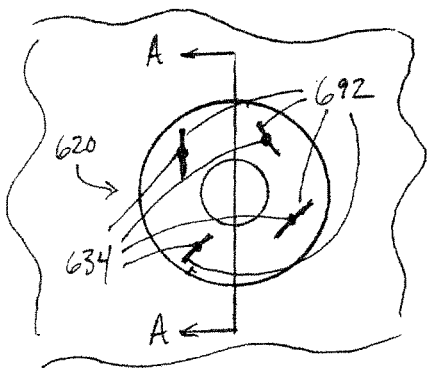

A variation on any embodiment of conduit comprised of any material involves the use of additional elements to secure the device in place relative to the tissue 657 adjacent to the device 620 and distribute any forces or physical loading of the device and tissue to prevent pull-through, dislodgement or migration of the device as shown in FIGS. 6A-D. This may be done using a suitable material, such as suture 691 (as illustrated in FIG. 6A) or T-tags 692 (FIG. 6C). The retaining and load-distributing material may be caused to go through holes or apertures 634 in the conduit retaining flanges, projecting rim, collar, or ring at the distal end 622 and/or the proximal end 625, and these holes or apertures may either be created when the retaining and load-distributing material (e.g. suture) is applied or they may be integrally designed into and manufactured as a feature of the device. Alternately, the retaining and load-distributing material (e.g. suture) may be arranged so that it encircles, captures or otherwise retains elements of the conduit.

Figure 7:
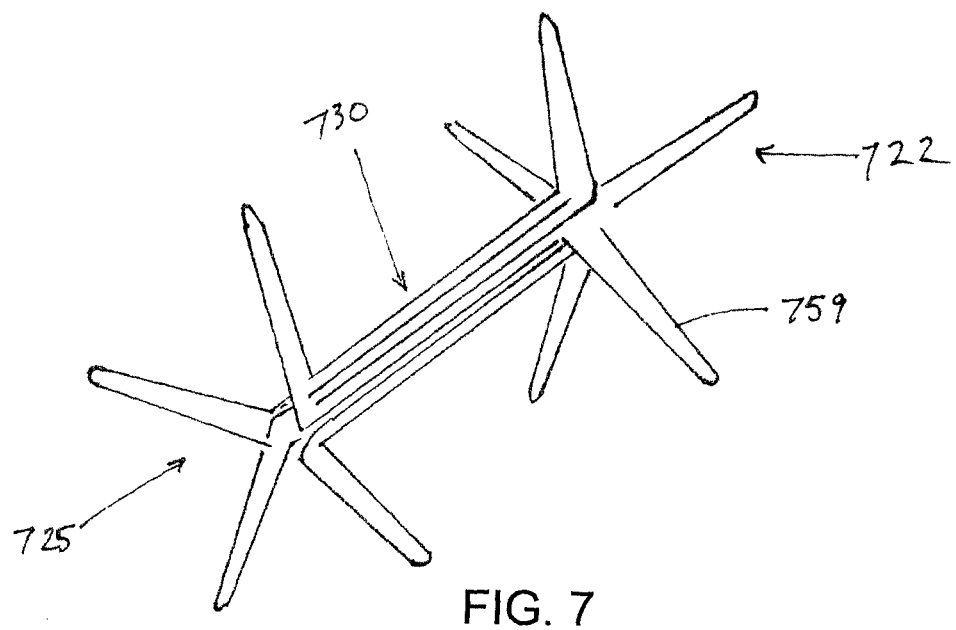
FIG. 7 illustrates another embodiment of the device comprised of bent wire.

Another embodiment of the conduit made from an elastic material in wireform. The wireform can be formed from a suitable shape memory elastic material such as nickel titanium alloy, also known as nitinol. The wire is configured or trained to assume the general shape of conduit as described throughout this specification, with a zig-zag pattern that runs in the longitudinal direction (end-to-end), as shown in FIG. 7. For delivery, the wire may be compressed, straightened, or otherwise reduced in overall size. In the deployed or final configuration, this embodiment incorporates at least a distal end 722 retaining feature having two or more radial projections extending from a central axis that runs along the length of the device (e.g., through a passageway, if a passageway is present), a proximal end 725 retaining feature having two ore more radial projections, and a tubular portion 730.

Figure 8:
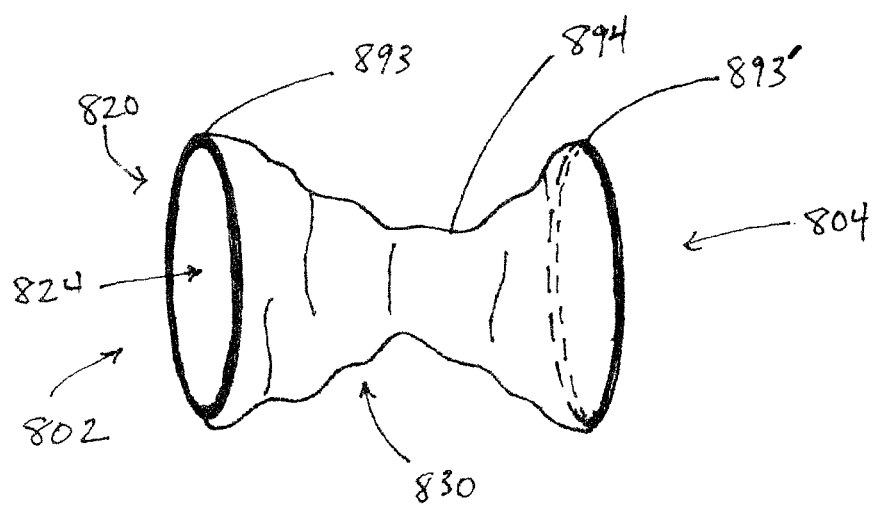
FIG. 8 illustrates another embodiment of the device comprised of distal and proximal supporting rings and a connecting portion of thin flexible material.

Yet another embodiment of a distal or proximal retaining feature for the conduit is shown in FIG. 8, and is comprised of a ring (or other shape that fully or partially encloses an area) of material 893 that may be constrained into a smaller profile for delivery, and that has a larger shape when not constrained. The material may be metallic, such as Nitinol, stainless steel or spring steel, or it may be elastomeric or plastic, such as silicone, urethane, etc. A ring 893, 893' may be positioned at the proximal end 802 of the device 820, the distal end 804 of the device 820, or both the proximal and distal ends. Attached to the ring is a compliant material 894 such as ePTFE or biocompatible fabric, sheet, or film, which comprises the tubular portion of a conduit, 830, and creates a lumen, aperture or passageway 824 therethrough.

Figure 9:
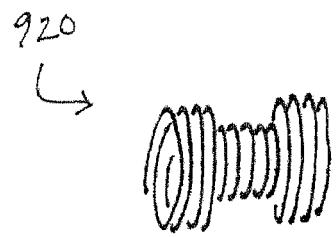
FIG. 9 illustrates another embodiment of the device comprised of wire with a variety of cross sections forming a coil.

FIG. 9 illustrates another embodiment of a conduit device, in which a coil is made of material with sufficient elasticity to allow it to be elongated into a straight wire without causing plastic deformation. Suitable materials include shape memory alloys, such as Nitinol, or other suitable shape memory materials. When not constrained and allowed to relax, the wire assumes the general shape of the conduit 920, and is comprised entirely of loops of coiled wire. The profile of the wire may be round, square, triangular, trapezoidal, polygonal, or any other profile shape which wire can be configured to have. In the case of a round profile, the wire is most easily manufacturable and obtainable. In the case of a square profile, the successive turns of the coil that together comprise the conduit may slide linearly relative to a neighboring turn of coil without opening a space through which material (e.g. bile, chyme) may flow. The device comprises a distal end having a radially extending section at a distal end and a proximal end with a neck therebetween having a radius less than the radius of one or both of the radially extending sections. Moreover, a passageway can be provided to provide fluid communication between the distal end and the proximal end.

Figure 10:
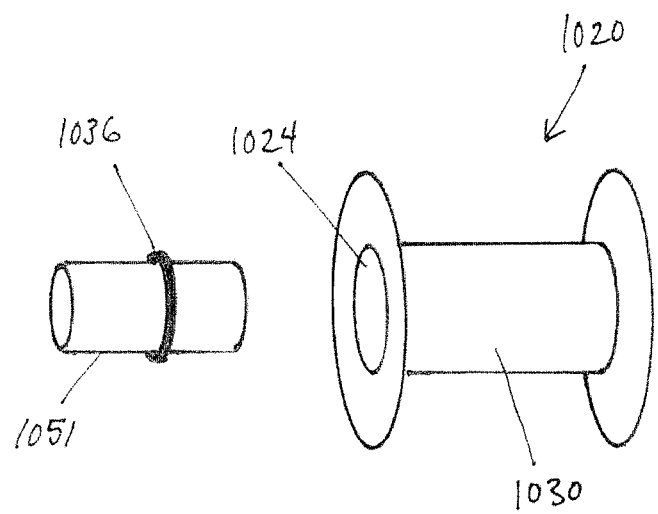
FIG. 10 illustrates an element that is insertable into the device adapted to provide a conduit between two body lumens.

Various embodiments may benefit from the insertion of an element 1051 into their inner lumen, aperture or passageway 1024, such as is illustrated in FIG. 10. The element may optionally include a feature that acts as a valve (e.g. a flap-, duckbill-, bicuspid-, tricuspid-, n-cuspid-, ball-, or other valve configuration) to control the flow of material between the gallbladder and the GI tract (e.g. a one-way valve, check valve, or a standard valve). The inserted element may serve to provide rigidity and/or support for the tubular portion 1030 so that its shape or configuration does not change in an undesirable way over the useful life of the device. The element may also serve to secure the conduit into position relative to the adjacent tissue, for example by expanding the device outward or otherwise increasing its outer dimensions, or alternately by incorporating a feature that otherwise serves to anchor or retain the inserted element (e.g. o-ring grooves, ridges, teeth, bumps, etc.). In cases where the inserted element provides structural integrity or support, the lumen or passageway 1024 of the conduit may entirely or partially lack structural integrity of its own and rely entirely on the inserted element to maintain a communication between the gallbladder and the GI tract (e.g. as shown in FIG. 8). In such cases, the element comprising the tubular portion of a conduit may be a sheath, flat tube/sleeve, balloon (inflated or deflated), coil, or any other shape into which the inserted element may be inserted. Optionally, the inserted element and the tubular element may be secured together by an additional retaining element 1036, such as an elastic band, an o-ring, or an adhesive.

Figure 11A:
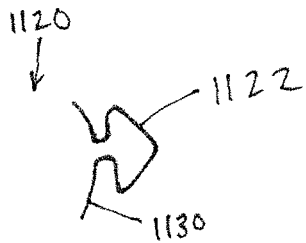
FIGS. 11A-G illustrate a number of SMA retaining feature configurations for the device and a scheme of arranging them on the device.
Figure 11B:
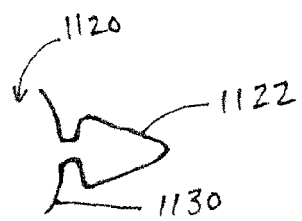
Figure 11C:
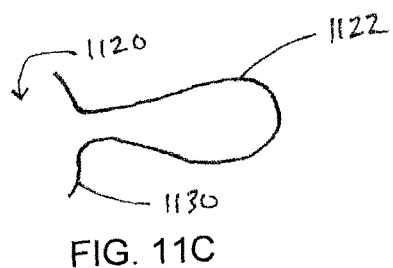
Figure 11D:
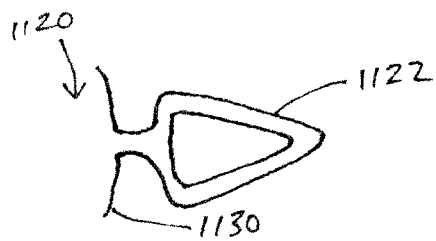
Figure 11E:
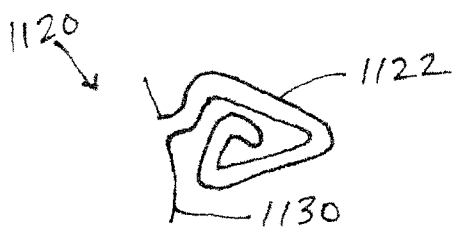
Figure 11F:
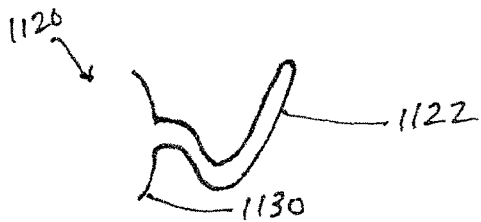
Figure 11G:
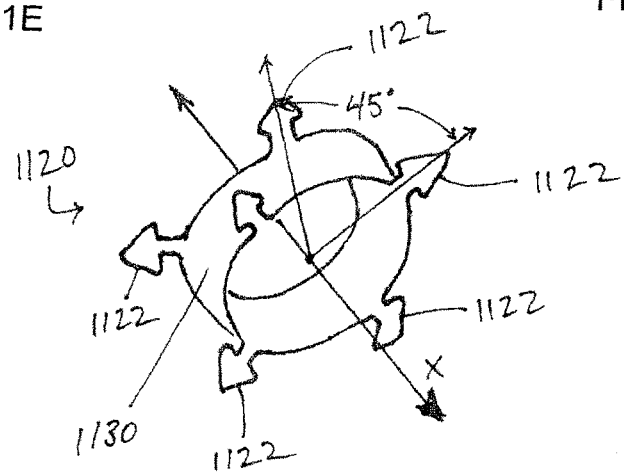
Figure 12A:
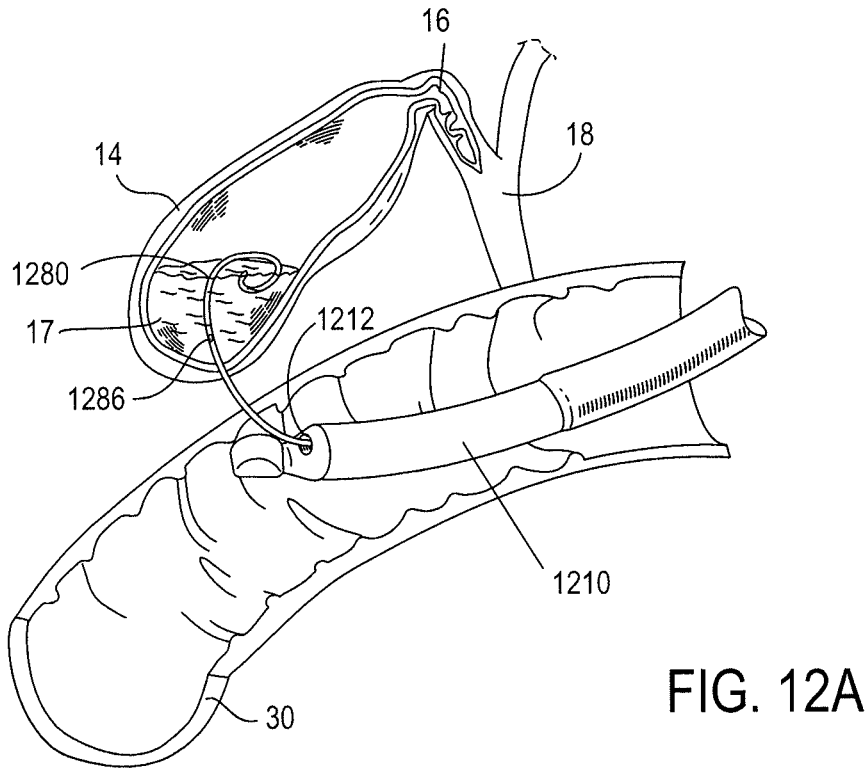
FIG. 12A-E illustrate delivery of the device according to the invention via a catheter.
Figure 12B:
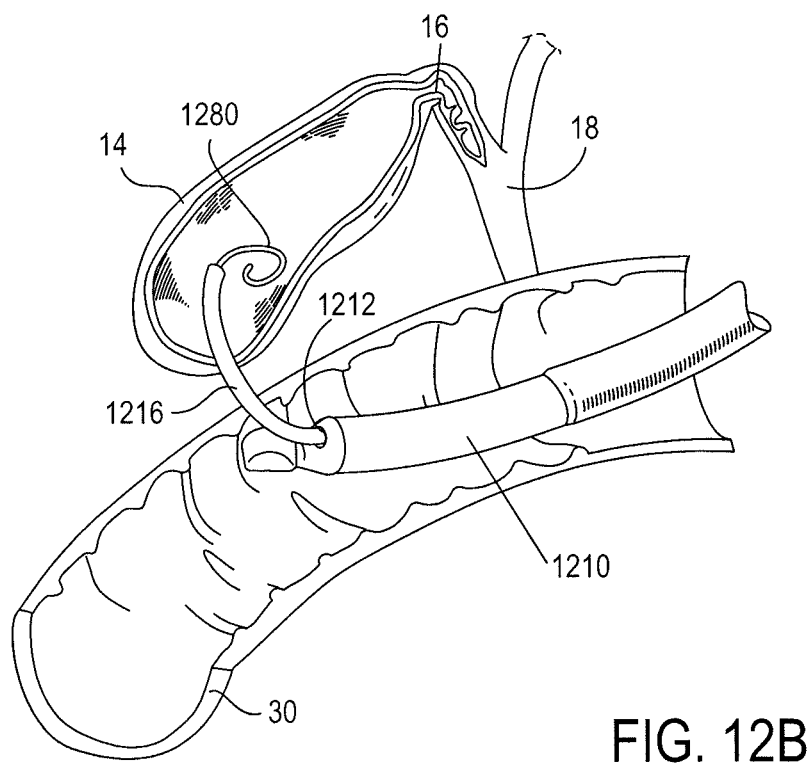
Figure 12C:
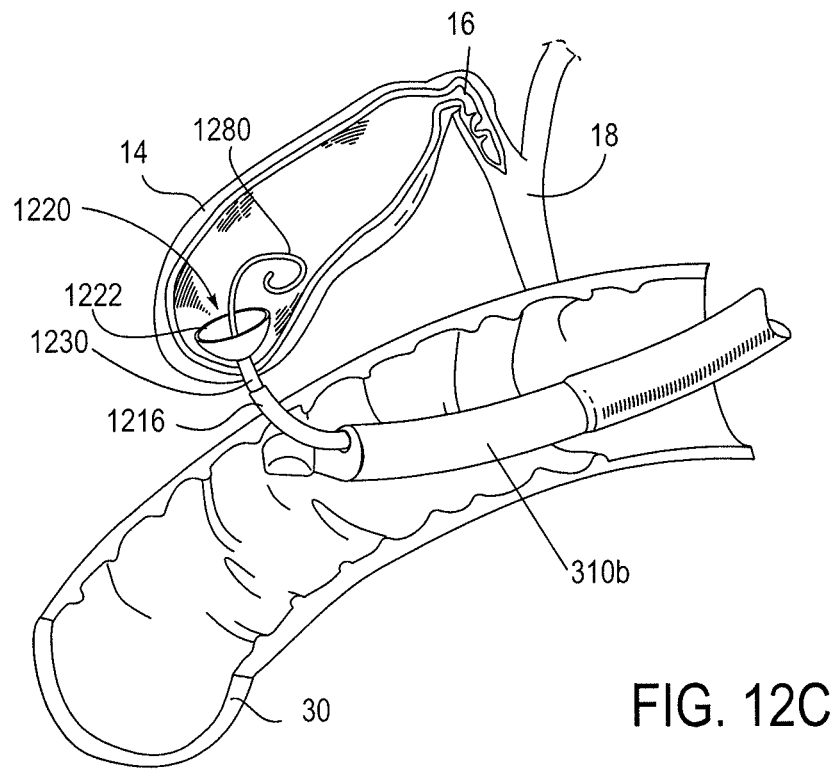
Figure 12D:
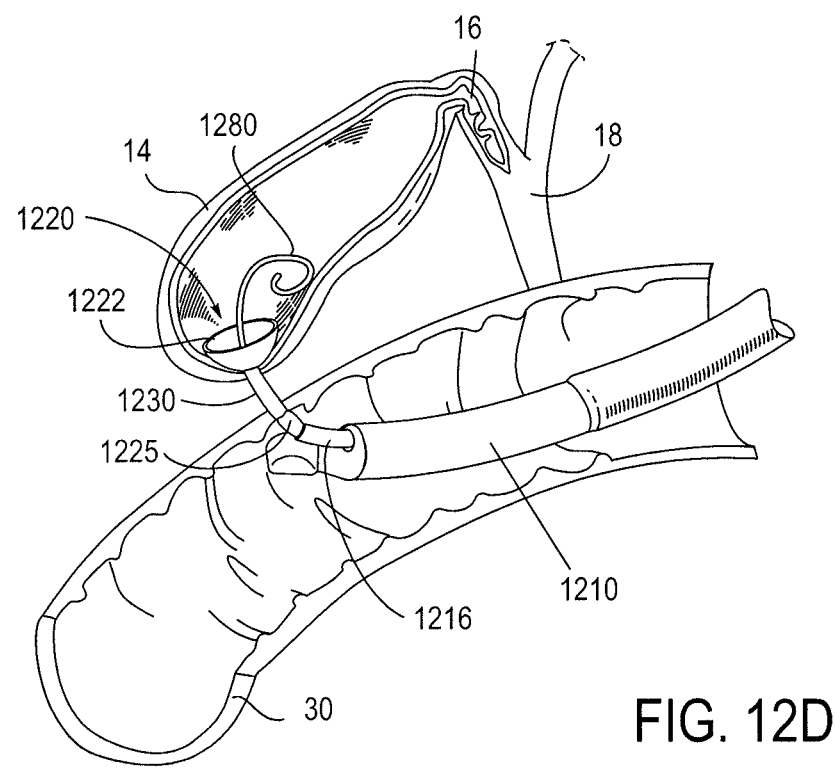
Figure 12E:
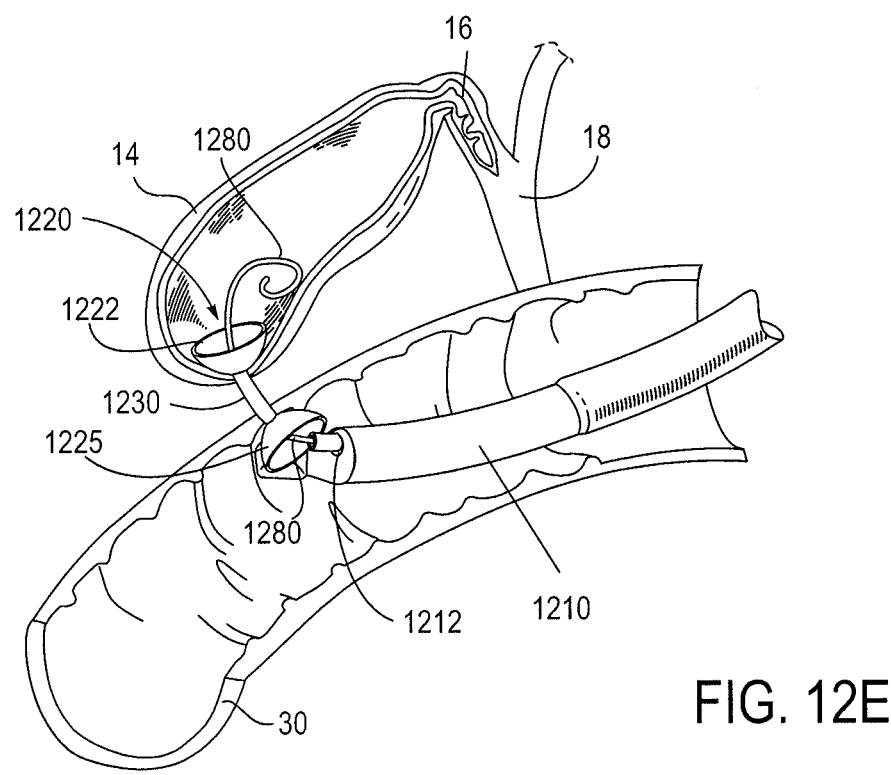

FIGS. 11A-G illustrates a number of embodiments of the conduit's retaining features 1122 located at either end of the conduit, which may be comprised of shape memory material (e.g. Nitinol) or other suitable elastic or superelastic material. This may be the case whether the tubular portion 1130 of the conduit 1120 is formed from the same or from different materials. Such retaining features may take on a number of shapes and configurations. FIGS. 11A through F show several of the many possible embodiments, in which the retaining features 1122 resemble fingers (e.g. elongate extensions). FIG. 11G shows how the fingers may be arranged in a radial star- or asterisk-like pattern from the ends of the conduit's tubular portion 1130. During delivery, the fingers are flexed in towards the central axis x of the tube 1130 to reduce the profile. Upon deployment, the fingers are allowed to spread outwards to function as retaining features. If such retaining features are incorporated on both ends of the tubular portion, the arrangements on either end may be rotated relative to each other to avoid pinching tissue held between them for the benefit of reducing the loading imparted to the tissue and reducing the potential for tissue necroses. This is illustrated in FIG. 11G, which shows a case where each end of the tube 1130 has four such retaining fingers, and the retaining fingers at the distal end are rotated 45 degrees relative to the retaining fingers at the proximal end of the tubular portion of the conduit. The number of degrees of rotation depends on the number of retaining features at either end, and may have either equal spacing (as illustrated in FIG. 11G) or variable spacing.

The conduit may be made of any suitable biocompatible material that is elastic and soft. Silicone is the preferred material. Other materials may optionally be used, e.g. polytetrafluoroethylene (PTFE), expanded PTFE, other members of the fluoropolymer family, urethanes, polyurethanes, and others. The materials can, for example, be soft at body temperature, with durometer typically in the range of 20-90 A. Softer materials are easier to deliver and reduce the risk of injury to adjacent tissue. A suitable material is, for example, soft enough to compress to a compact size for delivery and deployment.

Embodiments of retaining features may be comprised of compliant polymeric material (e.g. silicone). If they are comprised of soft, compliant materials, the retaining features can readily bend and deform to accommodate the passage of large items through the conduit formed between a first body lumen and a second body lumen, e.g. the gallbladder and the duodenum. Alternately, the retaining features may be formed from less compliant material or a metal (e.g. Nitinol or stainless steel). The retaining features may be formed integrally with other elements of the overall conduit device, such that the components are formed to act in a unified manner as a single component, or may be separate from the other elements of the overall conduit device. The retaining features may be incorporated into the overall assembly during manufacturing, or the parts may be installed by a clinician user prior to use in a patient or during deployment of the device within a patient.

The device, or other devices described herein, may also be comprised of a biodegradable, bioabsorbable, or resorbable material, in which case it may dissolve within the mammalian body within a desirable and useful length of time. This could eliminate the need for follow-up procedures to remove the device at the end of a course of treatment. Manufacturing the device from such a material may not prevent clinicians from actively removing it if the need arose, however. Rather, it would prevent the need to actively remove it in cases where no other treatment was required.

The conduit may be comprised of a single component and a single material, or it may be an assembly of different components, some of which may be of different materials that are integrally formed to act or perform in a unified manner once deployed. For instance, a conduit may be comprised of an SMA spring form, over which silicone (or another suitable polymer material) is molded. The spring form serves to lend the conduit structure and dimensional stability, while the silicone (or other polymer) outer shell creates soft surfaces which are unlikely to cause injury to tissue and facilitate sealing of the device in situ and prevent leaks. If SMA materials are used, their transition temperatures can be selected to be slightly below body temperature, so that they can be designed to hold one shape for delivery and deployment, and, after transitioning, they will have the desired shape(s) for optimizing the function of the conduit. Alternately, the SMA material may be used in its superelastic state.

Description of the Delivery Mechanisms:

Delivery of the conduit may be accomplished in a variety of ways.

An examplar delivery method is shown in FIG. 12. The examplar delivery method shown in FIGS. 12A through E involves using an endoscope 1210 to place one or more guidance elements 1280 (for example a needle, a guidewire, and/or a guidance catheter) between the access body lumen (e.g. the duodenum, stomach, or jejunum) and the gallbladder 14. In cases where a needle, a guidewire and/or a guidance catheter are used, a guidance catheter may be advanced in the patient's gastrointestinal tract at a target region or location, often but not necessarily within the working channel 1212 of an endoscope 1210, until the distal tip of the guiding catheter is proximal to the desired placement location for the device 1220. A needle may be advanced out of the distal end of the guiding catheter through the wall in the gastrointestinal tract, e.g. at a duodenum 30, continuing through the wall of the gallbladder 14, and into the lumen of the gallbladder. As an optional step, bile may be aspirated through the needle or any other guidance element 1280 to reduce the pressure within the gallbladder 14, reducing the risk of bile escaping the gallbladder within the peritoneum. To facilitate this, the guidance element (e.g. needle, guidewire, guidance catheter) may incorporate an aspiration port 1286, either distal or anywhere along a surface or wall. As another optional step, a guidewire may be inserted into the gallbladder lumen through the needle. In cases where a guidewire is used, the needle may be withdrawn once the guidewire has been inserted. When desirable, either the guidance catheter or a separate dilatation catheter, having an inflatable balloon, mechanical tissue expander, or other means of dilation on the distal portion thereof, may be advanced over the previously introduced needle or guidewire until the dilation element is properly positioned through the wall of the gastrointestinal tract and the wall of the gallbladder 14. Once in the desired position, the dilatation catheter may dilate the tissue around the catheter so that it is expanded to accommodate the device 1220. Generally, the diameter of the dilated puncture in the wall of the gallbladder 14 and gastrointestinal tract access lumen is slightly smaller than the outer diameter of the tubular portion 1230 of the device 1220 that will be inserted through the puncture. In one approach, the device 1220 may then be guided into position over the guidance element(s) 1280 (e.g. needle, guidewire, guidance catheter, delivery catheter) through the hole in the wall of the gastrointestinal tract and the wall of the gallbladder 14 to the desired depth. Once in the desired position, the device 1220 may be deployed and held in position by its retaining features 1222 and the adjacent tissue.

A delivery catheter for the conduit may be configured in a variety of ways. Persons of skill in the art will be familiar with the details of catheter construction, including variations of the proximal end and shaft region. See, for example, the following references:

| PAT. NO. | Title |
| --- | --- |
| 7,727,225 | Coaxial catheter systems for transference of medium |
| 7,722,629 | System and method for catheter-based septal defect repair |
| 7,717,936 | Device for loading an embolic protection filter into a catheter |
| 7,717,871 | System and method for site specific therapy |
| 7,704,245 | Large diameter delivery catheter/sheath |
| 7,704,223 | System and method for delivering a substance to a body cavity |
| 7,670,364 | Stent delivery system having stent securement apparatus |
| 7,647,891 | Method and apparatus for creating a pathway in an animal |
| 7,645,259 | Multi-function catheter and use thereof |
| 7,641,645 | Combination thrombolytic infusion catheter and dilator system |
| 7,634,319 | Method and anchor for medical implant placement, and method of anchor manufacture |

Figure 13A:
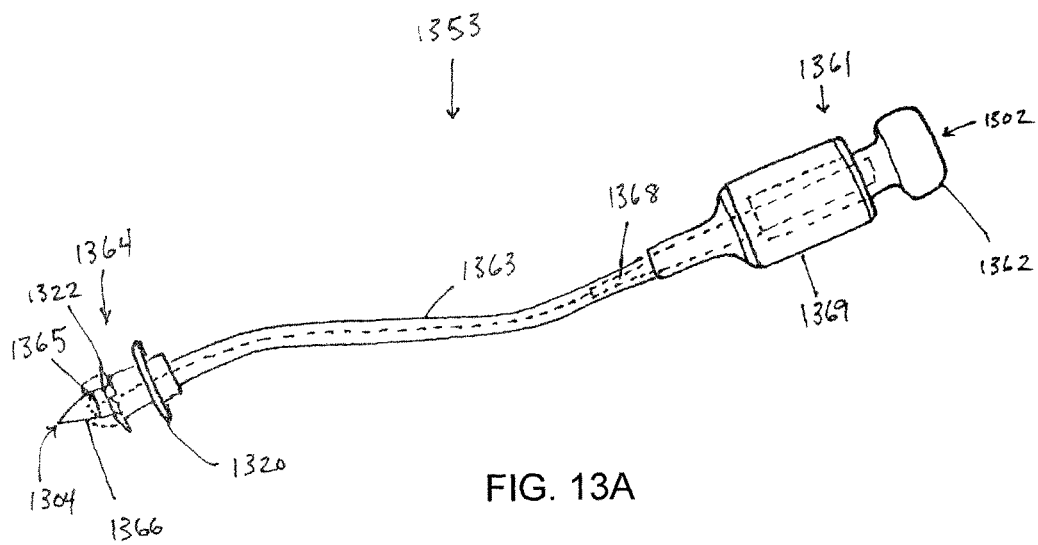
FIGS. 13A-B illustrate an embodiment of a delivery catheter for the device.
Figure 13B:
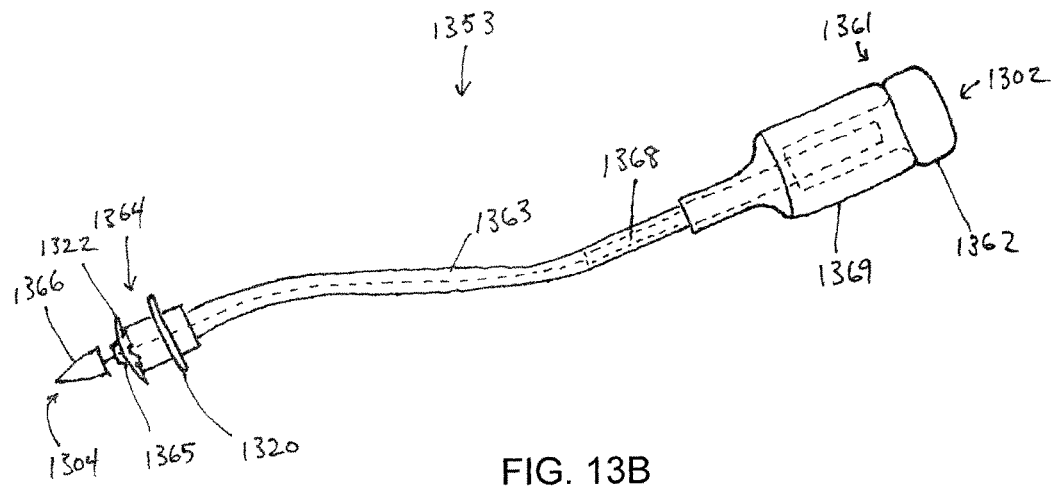

For purposes of appreciating this disclosure, an exemplar delivery catheter is illustrated in FIG. 13A, which shows a view of the entire delivery catheter system, which incorporates a control handle at the proximal end 1302, an elongate flexible shaft 1363 (the length of which is adequate for reaching the desired site in the access lumen, and may be longer or shorter than depicted herein) and a delivery element 1364 at the distal end 1304. The disclosure, however, focuses on details relating to the distal end. The proximal end control handle 1361 incorporates a pushable button element 1362 which moves a central pushrod 1368 relative to the control handle grip 1369 and the elongate shaft 1363 to actuate movable components incorporated in the delivery element 1364 at the distal end 1304. The delivery element incorporates two cone-shaped components, an inner cone 1365 and an outer cone 1366. Pushing the button 1362 in the handle 1361 pushes the outer cone 1366 forward and away from the inner cone 1365. The distal-most cone clamps the distal flange of the conduit (bending it forward and reducing its profile) against the proximal-most cone. Pushing the distal-most cone forward releases and unfurls the distal-most flange of the conduit (once it's been inserted through the walls and is where we want it to be deployed). A conduit 1320 is loaded onto the delivery element 1364 of the delivery catheter 1353, where the inner cone 1365 and outer cone 1366 clamp together over and secure the flared retaining features 1322 at the conduit's distal end. The configuration of the cones 1365 and 1366 also serve to position the distal flared retaining features 1322 forward and inward to reduce their profile and facilitate delivery to the implantation site, while the cone shape facilitates insertion in to the hole created between the gallbladder 14 and the access lumen in the GI tract. When the conduit has been inserted into the hole and is in the desired location, the delivery element 1364 may be actuated by pushing on the button 1362 in the handle 1361, which separates the cones 1365 and 1366 and deploys the distal retaining features 1322 of the conduit 1320. This is illustrated in FIG. 13B. With the distal retaining features 1322 holding the device securely in place, the proximal retaining feature 1322 retains the device in the access lumen (e.g. duodenum, stomach, or jejunum), and the delivery catheter 1353 may be withdrawn.

Figure 14:
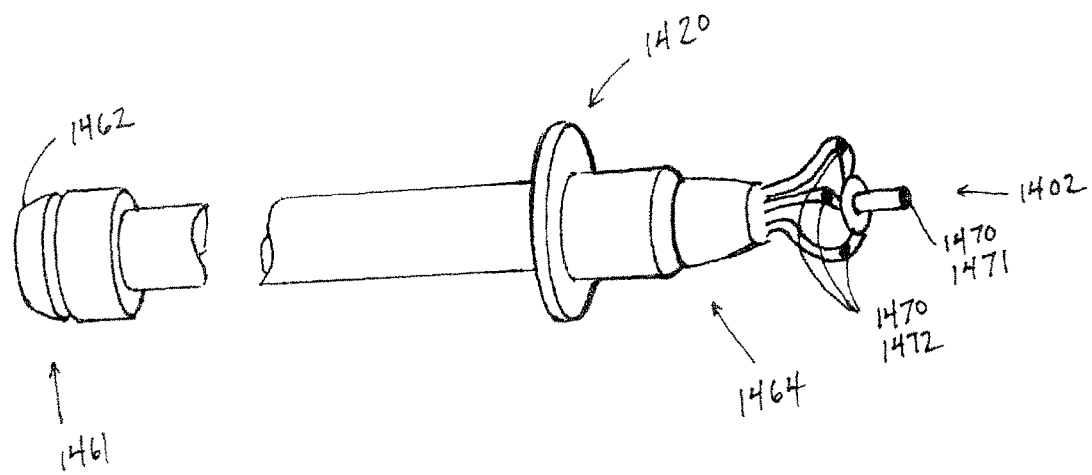
FIG. 14 illustrates another embodiment of a delivery catheter that incorporates electrosurgery electrodes.

Another embodiment of a delivery catheter is shown in FIG. 14. At the distal end of the delivery element 1402 this embodiment incorporates at least one electrosurgical electrode 1470 so that the hole in the wall of the access lumen (e.g. duodenum, stomach, jejunum, etc.) and gallbladder wall may be created and sized with the same instrument that delivers and deploys a conduit 1420. More than one electrosurgical electrode may be incorporated in the distal end of the delivery catheter, and may include a leading edge electrode 1471 and one or more radially arranged dilating electrodes 1472. The dilating electrodes may be configured to be positionable by the clinician (for example, by pushing or pulling the button 1462 at the handle 1461), so that the size of the resulting hole is selectable. Deployment of the conduit 1420 may then be performed using any suitable means and actions with the delivery element 1464.

Another embodiment of delivery catheter is shown in FIG. 15. In this embodiment, the distal end 1504 is configured in such a way that pulling back on a central member (e.g. a pull cable or wire) 1573 moves the distal end of the device 1504 relative to a coaxial sheath 1574. Attached to the coaxial sheath and the central member is one or more flexible members 1575, made from an elastic or superelastic material such as Nitinol, or alternately mechanically hinged so that large mechanical strain is not created. When the sheath 1574 and the central member 1573 are moved relative to each other, the flexible members 1575 expand outward, which can be used to anchor and retain the delivery catheter within a lumen, create a working volume within the gallbladder, and enable clinicians to pull back on the catheter to hold the wall of the gallbladder 14 and the access lumen (such as the duodenum, stomach, jejunum, etc.) in apposition. Further, if the flexible members 1575 may be configured so that further retractacting the central member 1573 causes the flexible members 1575 to double back and create an umbrella shape, which may then define a volume within which manipulations may be performed (a "work space"), such as deploying a conduit. Optionally, the flexible members may incorporate electrosurgical electrodes 1576 for cutting and dilating a hole into a desired configuration.

Figure 16:
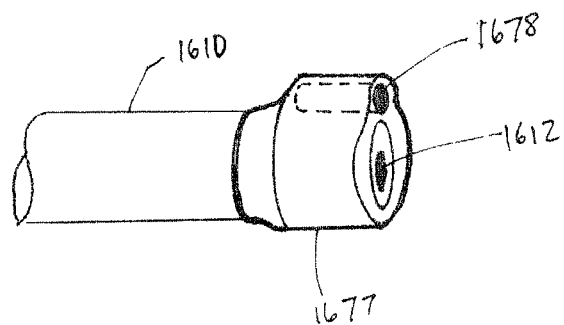
FIG. 16 illustrates an embodiment of a device that fits on the distal end of an endoscope that provides an additional tool channel or towing point.

FIG. 16 shows a device 1677 which may facilitate delivery by an endoscope 1610 of elements that are ill suited for delivery through the endoscope's tool channel 1612, or when a tool channel is otherwise occupied. This may be thought of as an adjunct tool channel, or in some cases, a towing point or "hitch", by means of which elements may be brought to a site by an endoscope and used without requiring repeated insertion and withdrawal of the endoscope or tools within the working channel of the endoscope. The device 1677 may be added at the distal end of the endoscope 1610 by means of clipping, bonding, or otherwise attaching, but preferably without or with only minimal modifications to the endoscope itself. The shape of the device is smooth in order to reduce or eliminate trauma to any tissue it contacts, and to reduce the likelihood of pinching or catching tissue. The device 1677 optionally incorporates at least one "hitching point" or auxiliary tool channel outlet 1678, to which elements (e.g. tubes, wires, catheters, etc.) may be attached and the distal end controlled with the bending section of the endoscope or with features incorporated into the elements, in much the same fashion that the position of tools are controlled when inserted into the endoscope's primary tool channel.

Figure 17:
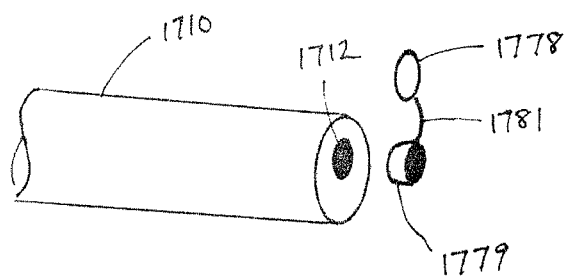
FIG. 17 illustrates another embodiment of a device that fits on the distal end of an endoscope that provides an additional tool channel or towing point.

Another embodiment of the device 1779 is shown in FIG. 17. This device is affixed to the distal tip of an endoscope 1710 at the distal outlet of the tool channel 1712. The device is configured as a thin ring, which is inserted partially or entirely into the outlet of the tool channel 1712 in order to retain and secure the device during a procedure. The device optionally incorporates at least one hitching point or auxiliary tool channel outlet 1778 on a member or stem 1781 that extends outward beyond the outer rim of the endoscope's distal tip. Elements such as tubes, wires, catheters, etc. may be attached to the hitching point or tool channel outlet, as described above.

Figure 18:
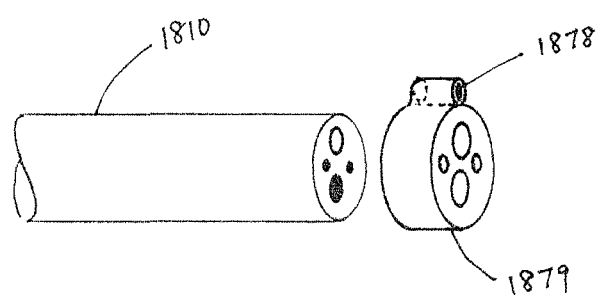
FIG. 18 illustrates another embodiment of a device that fits on the distal end of an endoscope that provides an additional tool channel or towing point.

Yet another embodiment of the device is shown in FIG. 18. In this embodiment, the device 1879 is configured as a cap that fits over the distal end of an endoscope 1810, with at least one hole in the portion covering the endoscope's distal end to accommodate the function of the endoscope's integral camera, illumination, tool channel, irrigation, aspiration, etc. The device 1879 attaches temporarily or permanently to the distal end of the endoscope 1810, and optionally incorporates at least one hitching point or auxiliary tool channel outlet 1878 at the perimeter. Elements such as tubes, wires, catheters, etc. may be attached to the hitching point(s) or tool channel outlet(s), as described above.

Description of Other Uses:

The techniques and devices described in this application may prove beneficial in applications beyond their initial use in the treatment of biliary disease.

For example, they may prove to be an effective mechanism of treating cholangitis (infection of the common bile duct 18). This condition is usually bacterial, and occurs when the bile duct is blocked by gallstones 20 or a tumor. Traditional treatment involves the insertion a stent or drainage catheter into the common bile duct 18 to allow bile to drain into the duodenum from locations above the obstruction. Placement of a conduit into the gallbladder 14 may allow for an alternate method of draining bile and/or other fluids into the duodenum. Any blockage in the common bile duct 18 between the entrance of the cystic duct and the duodenum may be treated in this way. See FIG. 2.

Another use of the devices and techniques described elsewhere in this application may be to create anastomoses between any body lumens in proximity to one another. This may include, but is not limited to: small bowel to small bowel anastomoses, small bowel to large bowel anastomoses, large bowel to large bowel anastomoses, and stomach to small bowel anastomoses. Additionally, creating a conduit between lumens within the GI system, such as between the stomach and other body lumens, esophagus and other body lumens, duodenum and other body lumens, etc., may be useful and effective for treating and/or managing obesity.

Another use of the devices and techniques described herein is for drainage of any body lumen into another body lumen in proximity, for example, the drainage of pancreatic pseudocysts.

Kits:

The devices disclosed herein can be provided within suitable packaging in kit form as will be appreciated by those skilled in the art. The kits can include one or more devices, one or more components useful for delivering the devices, and one or more pharmacological agents useful in performing the operation to deliver the device or devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A device for treating biliary disease comprising:
a component configured for establishing fluid communication between a gallbladder and a target location within a gastrointestinal tract of a mammal, the component having a proximal end and a distal end with a lumen extending therethrough, a tubular portion with a proximal retaining feature on an outer surface of the tubular portion and a distal retaining feature on the outer surface of the tubular portion, wherein the proximal retaining feature has a disc shape and the distal retaining feature has a plurality of radially extending elements projecting outward therefrom, wherein the disc shape has a curved edge such that the device is atraumatic to adjacent tissue, wherein the tubular portion and the retaining features comprise dissimilar materials, and wherein the tubular portion comprises soft durometer molded silicone material with durometer in a range of 20-90 A.

2. The device of claim 1 wherein the device is formed from a bioresorbable material.

3. The device of claim 1 wherein the device is removable.

4. The device of claim 1 wherein the device is expandable.

5. The device of claim 1 wherein a cross-sectional area of the device is variable along a length.

6. The device of claim 1 wherein the device is configured for deployment by at least one of an endoscope, a needle, a guidewire, a guidance catheter, and a dilatation catheter.

7. The device of claim 1 further comprising a flareable end.

8. The device of claim 1 wherein the component has one or more clips configured to secure the component at one or more positions.

9. The device of claim 1 further comprising one or more fenestrations.

10. The device of claim 1 wherein the device is configured from one or more wires.

11. The device of claim 1 wherein at least one of the distal retaining feature and the proximal retaining feature extend from the tubular portion and curve back toward the tubular portion.

12. A biliary disease treatment device comprising:
a component configured for establishing fluid communication between a gallbladder and a target location within a gastrointestinal tract of a mammal, the component having a proximal end and a distal end with a lumen extending therethrough, a tubular portion with a proximal retaining feature on an outer surface of the tubular portion and a distal retaining feature on the outer surface of the tubular portion, configured to be delivered by an endoscope to a gastrointestinal site in proximity to a gallbladder, wherein the proximal retaining feature has a disc shape and the distal retaining feature has a plurality of radially extending elements projecting outward therefrom, wherein the disc shape has a curved edge such that the device is atraumatic to adjacent tissue, wherein the tubular portion and the retaining features comprise dissimilar materials, and wherein the tubular portion comprises soft durometer molded silicone material with durometer in a range of 20-90 A.

13. A method of delivering a device to treat biliary disease comprising:
using an endoscope to place at least one of a guidewire, a needle, a guidance catheter, and a dilatation catheter between an access lumen in a body and a gallbladder;
inserting a delivery catheter over the at least one of guidewire, needle, guidance catheter, and dilatation catheter and into the gallbladder;
delivering a component configured for establishing fluid communication between a gallbladder and a target location within a gastrointestinal tract of a mammal, the component having a proximal end and a distal end with a lumen extending therethrough, a tubular portion with a proximal retaining feature on an outer surface of the tubular portion and a distal retaining feature on the outer surface of the tubular portion, wherein the proximal retaining feature has a disc shape and the distal retaining feature has a plurality of radially extending elements projecting outward therefrom, wherein the disc shape has a curved edge such that the component is atraumatic to adjacent tissue, wherein the tubular portion and the retaining features comprise dissimilar materials, and wherein the tubular portion comprises soft durometer molded silicone material with durometer in a range of 20-90 A; and
positioning the component between the access lumen in the body and the gallbladder to create a lumen therebetween.

14. The method of claim 13 further comprising the step of passively retaining a distal end of the guidewire in the gallbladder while the guidewire is used to deliver additional elements.

15. The method of claim 13 further comprising delivering a substance to the gallbladder via the created lumen.

16. A device for treating biliary disease comprising:
a component configured for establishing fluid communication between a gallbladder and a target location within a gastrointestinal tract of a mammal, the component having a proximal end and a distal end with a lumen extending therethrough, a tubular portion with a proximal retaining feature extending radially beyond an outer surface of the tubular portion, and a distal retaining feature extending radially beyond the outer surface of the tubular portion, wherein the proximal retaining feature has a disc shape and the distal retaining feature has a plurality of radially extending elements projecting outward therefrom, wherein the disc shape has a curved edge such that the device is atraumatic to adjacent tissue, wherein the tubular portion and the retaining features comprise dissimilar materials, and wherein the tubular portion comprises soft durometer molded silicone material with durometer in a range of 20-90 A.

17. The device of claim 1, wherein the plurality of radially extending elements are divided into separate segments.

18. The device of claim 1, wherein the retaining features comprise at least one of silicone, urethane, Nitinol, and stainless steel.

* * * * *

UNITED STATES PATENT AND TRADEMARK OFFICE
CERTIFICATE OF CORRECTION

PATENT NO. : 9,901,347 B2
APPLICATION NO. : 12/791816
DATED : February 27, 2018
INVENTOR(S) : Van Dam et al.

Page 1 of 1

It is certified that error appears in the above-identified patent and that said Letters Patent is hereby corrected as shown below:

In the Specification

In Column 1, Line 4, delete "CROSS-REFERENCE" and insert -- CROSS-REFERENCE TO RELATED APPLICATIONS --, therefor.

In Column 1, Line 29, delete "their entirety." and insert -- their entireties. --, therefor.

In Column 4, Line 34, delete "cholangiopanctreatograpy" and insert -- cholangiopancreatography --, therefor.

In Column 4, Line 59, delete "cholangiopancreatograpy)" and insert -- cholangiopancreatography) --, therefor.

In Column 10, Line 12, delete "illustrates another" and insert -- illustrate another --, therefor.

In Column 10, Line 14, delete "illustrates an" and insert -- illustrate an --, therefor.

In Column 10, Line 30, delete "FIG. 12A-E" and insert -- FIGS. 12A-E --, therefor.

In Column 10, Line 35, delete "illustrates another" and insert -- illustrate another --, therefor.

In Column 14, Line 9, delete "ore" and insert -- or --, therefor.

In Column 15, Line 8, delete "illustrates a" and insert -- illustrate a --, therefor.

Figure 15A:
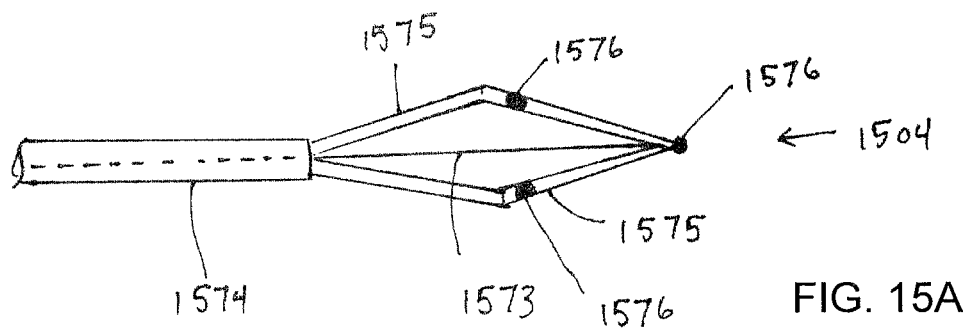
FIGS. 15A-C illustrates another embodiment of a delivery catheter that incorporates a retaining and space-making element at the distal tip.
Figure 15B:
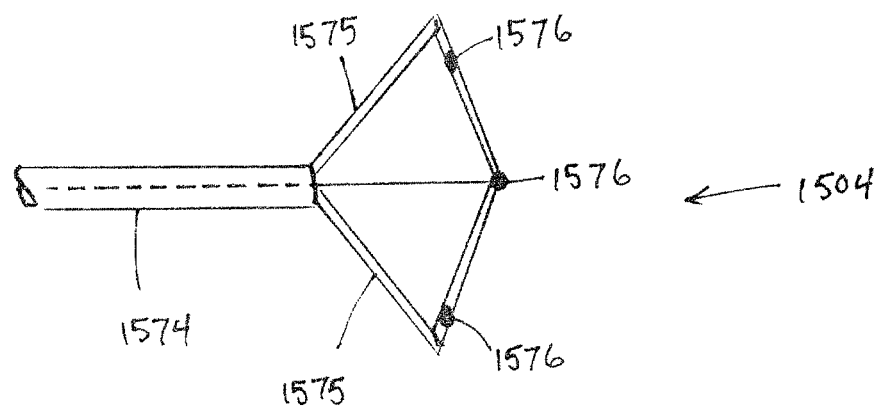
Figure 15C:
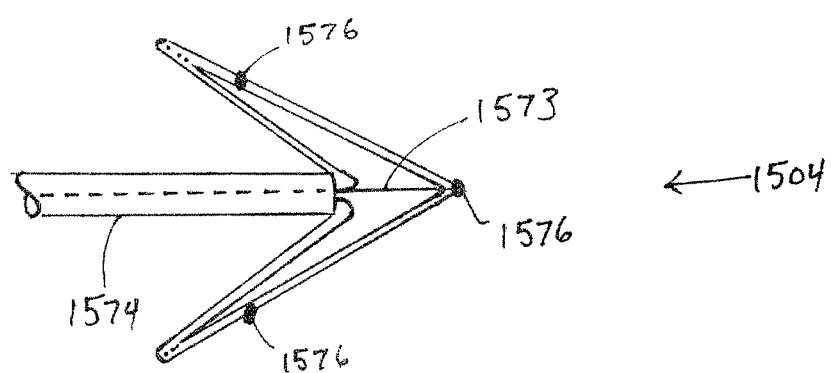

In Column 18, Line 40, delete "FIG. 15." and insert -- FIG. 15A-C. --, therefor.

Signed and Sealed this
First Day of May, 2018

Andrei Iancu
*Director of the United States Patent and Trademark Office*